United States Patent
Gurcan et al.

(10) Patent No.: US 12,315,143 B2
(45) Date of Patent: May 27, 2025

(54) SYSTEM AND METHOD OF USING RIGHT AND LEFT EARDRUM OTOSCOPY IMAGES FOR AUTOMATED OTOSCOPY IMAGE ANALYSIS TO DIAGNOSE EAR PATHOLOGY

(71) Applicant: Ohio State Innovation Foundation, Columbus, OH (US)

(72) Inventors: Metin Gurcan, Winston-Salem, NC (US); Aaron Moberly, Columbus, OH (US)

(73) Assignee: Ohio State Innovation Foundation, Columbus, OH (US)

(*) Notice: Subject to any disclaimer, the term of this patent is extended or adjusted under 35 U.S.C. 154(b) by 634 days.

(21) Appl. No.: 17/545,691

(22) Filed: Dec. 8, 2021

(65) Prior Publication Data
US 2022/0261987 A1    Aug. 18, 2022

Related U.S. Application Data

(60) Provisional application No. 63/146,903, filed on Feb. 8, 2021.

(51) Int. Cl.
| | |
|---|---|
| *G06T 7/00* | (2017.01) |
| *A61B 1/227* | (2006.01) |
| *A61B 5/103* | (2006.01) |
| *A61B 5/12* | (2006.01) |
| *G06V 10/40* | (2022.01) |
| *G06V 10/764* | (2022.01) |
| *G06V 10/80* | (2022.01) |
| *G06V 10/82* | (2022.01) |

(52) U.S. Cl.
CPC ............ *G06T 7/0012* (2013.01); *A61B 1/227* (2013.01); *A61B 5/1032* (2013.01); *A61B 5/12* (2013.01); *G06V 10/40* (2022.01); *G06V 10/764* (2022.01); *G06V 10/806* (2022.01); *G06V 10/82* (2022.01); *G06T 2207/20081* (2013.01); *G06T 2207/10016* (2013.01); *G06T 2207/20084* (2013.01); *G06T 2207/20212* (2013.01); *G06V 2201/03* (2022.01)

(58) Field of Classification Search
None
See application file for complete search history.

(56) References Cited

U.S. PATENT DOCUMENTS

| | | | |
|---|---|---|---|
| 11,615,604 B2 * | 3/2023 | Chung | A61B 5/0042 |
| | | | 382/128 |
| D991,279 S * | 7/2023 | Yue | D14/486 |
| 2009/0185191 A1 | 7/2009 | Boppart et al. | |

(Continued)

OTHER PUBLICATIONS

OtoMatch: Content-based eardrum image retrieval using deep learning SedaCamalan ID 3 1, MuhammadKhalidKhanNiazi1, AaronC. Moberly2, Theodoros Tekanos et al. (Year: 2020).*

(Continued)

*Primary Examiner* — Nancy Bitar
(74) *Attorney, Agent, or Firm* — Meunier Carlin & Curfman LLC

(57) ABSTRACT

Disclosed herein are systems and methods to detect a wide range of eardrum abnormalities by using high-resolution otoscope images of both a left eardrum and a right eardrum of a subject and report the condition of each of the eardrums as "normal" or "abnormal."

30 Claims, 11 Drawing Sheets

(56) References Cited

U.S. PATENT DOCUMENTS

2019/0216308 A1\* 7/2019 Senaras .................. A61B 1/227
2020/0069167 A1 3/2020 Andreassen et al.

OTHER PUBLICATIONS

International Search Report and Written Opinion issued for Application No. PCT/US2021/062401, dated Feb. 24, 2022, 10 pages.
Marin, Karina Cristina, et al. "Application of a finite element model in the diagnosis process of middle ear pathologies." Rom J Morphol Embryol 55.4 (2014): 1511-1514.
Camalan, Seda, et al. "OtoPair: Combining right and left eardrum otoscopy images to improve the accuracy of automated image analysis." Applied Sciences 11.4 (2021): 1831.
L. K. Cole, "Otoscopic evaluation of the ear canal," The Veterinary clinics of North America. Small animal practice, vol. 34, No. 2, pp. 397-410, 2004.
M. E. Pichichero and M. D. Poole, "Comparison of performance by otolaryngologists, pediatricians, and general practioners on an otoendoscopic diagnostic video examination," International journal of pediatric otorhinolaryngology, vol. 69, No. 3, pp. 361-366, 2005.
L. S. Goggin, R. H. Eikelboom, and M. D. Atlas, "Clinical decision support systems and computer-aided diagnosis in otology," Otolaryngology—Head and Neck Surgery, vol. 136, No. 4_suppl, pp. s21-s26, 2007.
M. A. Khan et al., "Automatic detection of tympanic membrane and middle ear infection from oto-endoscopic images via convolutional neural networks," Neural Networks, 2020, 384-394.
A. Kuruvilla, N. Shaikh, A. Hoberman, and J. Kovačević, "Automated diagnosis of otitis media: vocabulary and grammar," International Journal of Biomedical Imaging, vol. 2013, 2013, 327515, 15 pages.
E. Başaran, Z. Cömert, and Y. Çelik, "Convolutional neural network approach for automatic tympanic membrane detection and classification," Biomedical Signal Processing and Control, vol. 56, p. 101734, 2020.
M. S. Kasher, "Otitis Media Analysis—An Automated Feature Extraction and Image Classification System," 2018, 60 pages.
E. Başaran, Z. Cömert, A. Şengür, Ü. Budak, Y. Çelik, and M. Toğaçar, "Chronic Tympanic Membrane Diagnosis based on Deep Convolutional Neural Network," in 2019 4th International Conference on Computer Science and Engineering (UBMK), 2019: IEEE, pp. 1-4.
H. C. Myburgh, S. Jose, D. W. Swanepoel, and C. Laurent, "Towards low cost automated smartphone-and cloud-based otitis media diagnosis," Biomedical Signal Processing and Control, vol. 39, pp. 34-52, 2018.
L. Monasta et al., "Burden of disease caused by otitis media: systematic review and global estimates," PloS one, vol. 7, No. 4, p. e36226, 2012.
D. Cha, C. Pae, S.-B. Seong, J. Y. Choi, and H.-J. Park, "Automated diagnosis of ear disease using ensemble deep learning with a big otoendoscopy image database," EBioMedicine, vol. 45, pp. 606-614, 2019.
C. Senaras et al., "Autoscope: automated otoscopy image analysis to diagnose ear pathology and use of clinically motivated eardrum features," in Medical Imaging 2017: Computer-Aided Diagnosis, 2017, vol. 10134: International Society for Optics and Photonics, p. 101341X.
H. Binol et al., "Decision fusion on image analysis and tympanometry to detect eardrum abnormalities," in Medical Imaging 2020: Computer-Aided Diagnosis, 2020, vol. 11314: International Society for Optics and Photonics, p. 113141M.
C.-K. Shie, H.-T. Chang, F.-C. Fan, C.-J. Chen, T.-Y. Fang, and P.-C. Wang, "A hybrid feature-based segmentation and classification system for the computer aided self-diagnosis of otitis media," in 2014 36th Annual International Conference of the IEEE Engineering in Medicine and Biology Society, 2014: IEEE, pp. 4655-4658.
M. Viscaino, J. C. Maass, P. H. Delano, M. Torrente, C. Stott, and F. Auat Cheein, "Computer-aided diagnosis of external and middle ear conditions: A machine learning approach," Plos one, vol. 15, No. 3, p. e0229226, 2020.
J. Seok, J.-J. Song, J.-W. Koo, H. C. Kim, and B. Y. Choi, "The semantic segmentation approach for normal and pathologic tympanic membrane using deep learning," BioRxiv, p. 515007, 2019.
H. Binol et al., "Digital otoscopy videos versus composite images: A reader study to compare the accuracy of ENT physicians," The Laryngoscope, 2020.
H. Binol et al., "SelectStitch: automated frame segmentation and stitching to create composite images from Otoscope video clips," Applied Sciences, vol. 10, No. 17, p. 5894, 2020.
S. Camalan et al., "OtoMatch: Content-based eardrum image retrieval using deep learning," Plos one, vol. 15, No. 5, p. e0232776, 2020.
C.-K. Shie, H.-T. Chang, F.-C. Fan, C.-J. Chen, T.-Y. Fang, and P.-C. Wang, "A hybrid feature-based segmentation and classification system for the computer aided self-diagnosis of otitis media," in Engineering in Medicine and Biology Society (EMBC), 36th Annual International Conference of the IEEE, 2014 2014, pp. 4655-4658.
I. Mironică, C. Vertan, and D. C. Gheorghe, "Automatic pediatric otitis detection by classification of global image features," in 2011 E-Health and Bioengineering Conference (EHB), 2011: IEEE, pp. 1-4.
E. Başaran, A. Şengür, Z. Cömert, Ü. Budak, Y. Çelik, and S. Velappan, "Normal and Acute Tympanic Membrane Diagnosis based on Gray Level Co-Occurrence Matrix and Artificial Neural Networks," in 2019 International Artificial Intelligence and Data Processing Symposium (IDAP), 2019: IEEE, pp. 1-6.
A. Kuruvilla, N. Shaikh, A. Hoberman, and J. Kovačević, "Automated Diagnosis of Otitis Media: Vocabulary and Grammar," (in en), International Journal of Biomedical Imaging, pp. 1-15, 2013 2013, doi: 10.1155/2013/327515.
C. Senaras et al., "Detection of eardrum abnormalities using ensemble deep learning approaches," in Medical Imaging 2018: Computer-Aided Diagnosis, 2018, vol. 10575: International Society for Optics and Photonics, p. 105751A.
J. Y. Lee, S.-H. Choi, and J. W. J. A. S. Chung, "Automated Classification of the Tympanic Membrane Using a Convolutional Neural Network," vol. 9, No. 9, p. 1827, 2019.
L. G. Brown, "A survey of image registration techniques," ACM computing surveys (CSUR), vol. 24, No. 4, pp. 325-376, 1992.
S. Mambo, Y. Hamam, B. van Wyk, K. Djouani, and P. Siarry, "A review on medical image registration techniques," World Academy of Science, Engineering and Technology International Journal of Computer and Information Engineering, vol. 12, No. 1, 2018.
X. Huang, J. Ren, G. Guiraudon, D. Boughner, and T. M. Peters, "Rapid dynamic image registration of the beating heart for diagnosis and surgical navigation," IEEE transactions on medical imaging, vol. 28, No. 11, pp. 1802-1814, 2009.
K. Miller et al., "Modelling brain deformations for computer-integrated neurosurgery," International Journal for Numerical Methods in Biomedical Engineering, vol. 26, No. 1, pp. 117-138, 2010.
N. Strehl, S. Tomei, J. Rosenman, and S. Joshi, "Large deformation 3D image registration in image-guided radiation therapy."
D. Maksimov et al., "Graph-matching based CTA," IEEE transactions on medical imaging, vol. 28, No. 12, pp. 1940-1954, 2009.
A. Roche, X. Pennec, G. Malandain, and N. J. I. t. o. m. i. Ayache, "Rigid registration of 3-D ultrasound with MR images: a new approach combining intensity and gradient information," vol. 20, No. 10, pp. 1038-1049, 2001.
J.-P. Thirion, "Non-rigid matching using demons," in Proceedings CVPR IEEE Computer Society Conference on Computer Vision and Pattern Recognition, 1996: IEEE, pp. 245-251.
A. Keikhosravi, B. Li, Y. Liu, and K. W. Eliceiri, "Intensity-based registration of bright-field and second-harmonic generation images of histopathology tissue sections," Biomedical Optics Express, vol. 11, No. 1, pp. 160-173, 2020.
M. Styner, C. Brechbuhler, G. Szckely, and G. Gerig, "Parametric estimate of intensity inhomogeneities applied to MRI," IEEE transactions on medical imaging, vol. 19, No. 3, pp. 153-165, 2000.

(56) References Cited

OTHER PUBLICATIONS

D.-J. Kroon, "Multimodality non-rigid demon algorithm image registration," MatlabCentral, www.mathworks.com/matlabcentral/fileexchange/21451-multimodality-non-rigid-demon-algorithm-imageregistration, 2008.

L. Breiman, "Bagging predictors," Machine learning, vol. 24, No. 2, pp. 123-140, 1996.

Mitchell W. Matthew, "Bias of the Random Forest out-of-bag (OOB) error for certain input parameters," Open Journal of Statistics, vol. 2011, 2011.

G. James, D. Witten, T. Hastie, and R. Tibshirani, An introduction to statistical learning. Springer, 2013. 441 pages.

R. G. von Gioi, J. Jakubowicz, J.-M. Morel, and G. Randall, "LSD: A fast line segment detector with a false detection control," IEEE transactions on pattern analysis and machine intelligence, vol. 32, pp. 722-732, 2010.

H. Bay, T. Tuytelaars, and L. Van Gool, "Surf: Speeded up robust features," Computer vision—ECCV 2006, pp. 404-417, 2006.

D. G. Lowe, "Distinctive image features from scale-invariant keypoints," International journal of computer vision, vol. 60, pp. 91-110, 2004.

E. Rublee, V. Rabaud, K. Konolige, and G. Bradski, "ORB: An efficient alternative to SIFT or SURF," in Computer Vision (ICCV), 2011 IEEE International Conference on, 2011, pp. 2564-2571.

M. A. Fischler and R. C. Bolles, "Random sample consensus: a paradigm for model fitting with applications to image analysis and automated cartography," Communications of the ACM, vol. 24, pp. 381-395, 1981.

K. He, X. Zhang, S. Ren, and J. Sun, "Deep residual learning for image recognition," in Proceedings of the IEEE Conference on Computer Vision and Pattern Recognition, 2016, pp. 770-778.

C. Szegedy, V. Vanhoucke, S. Ioffe, J. Shlens, and Z. Wojna, "Rethinking the inception architecture for computer vision," in Proceedings of the IEEE Conference on Computer Vision and Pattern Recognition, 2016, pp. 2818-2826.

C. Szegedy, S. Ioffe, V. Vanhoucke, and A. Alemi, "Inception-v4, inception-resnet and the impact of residual connections on learning," arXiv preprint arXiv:1602.07261, 2016. 4278-4284.

European Patent Office. Extended European Search Report. Issued in EP Application No. 21925074.3. Nov. 22, 2024. 12 pages.

* cited by examiner

SYSTEM AND METHOD OF USING RIGHT AND LEFT EARDRUM OTOSCOPY IMAGES FOR AUTOMATED OTOSCOPY IMAGE ANALYSIS TO DIAGNOSE EAR PATHOLOGY

CROSS-REFERENCE TO RELATED APPLICATIONS

This application claims priority to and benefit of U.S. provisional patent application 63/146,903 filed Feb. 8, 2021, which is fully incorporated by reference and made a part hereof.

GOVERNMENT SUPPORT CLAUSE

This invention was made with government support under grant number R21 DC016972 awarded by the National Institutes of Health. The government has certain rights in the invention.

BACKGROUND

Ear infections, specifically acute infections of the middle ear (acute otitis media), are the most commonly treated childhood disease and account for approximately 20 million annual physician visits in the U.S. alone.

Ear diseases are one of the diseases that can easily be treated when diagnosed at the right time, and when appropriate treatment methods are applied. Otherwise, ear diseases may cause hearing loss or other complications. An otoscopic examination is one of the most basic and common tools used to examine the ear canal and eardrum (tympanic membrane, TM) [1, 2]. With the help of otoscopic examination and clinical features, perforation of TM, cholesteatoma, acute otitis media (AOM), and chronic otitis media (COM) can be diagnosed by otolaryngologists and pediatricians. However, an examination by an experienced and skillful physician may not always be possible. To help physicians who lack the same otoscopy experience, computer-aided diagnosis (CAD) systems may be useful [3].

Most CAD systems use a classification method to determine whether the middle ear has an infection [4-8] because otitis media (OM) is one of the most common diseases for children under the age of five years [9, 10]. Other ear diseases such as retraction, perforation, and tympanosclerosis are classified as abnormal eardrum images against normal eardrum images by the automated CAD system [11-13]. In addition to classification methods, there are also approaches to segment and classify the TM on otoscopic images [14-16]. Recently, composite images, which are created by selecting certain otoscopy video frames and stitching them together, are also used to increase the probability of detecting ear pathology [17, 18]. US PG-Patent Publication No. US 2019/0216308 A1, published Jul. 18, 2019, which is fully incorporated by reference, is an example of a content-based image retrieval (CBIR) system, is also a good example of a CAD system designed to help physicians [19].

Generally, CAD approaches for TM analysis, which are used to classify and/or segment the ear-drum, can be collected under two categories: hand-crafted features-based and deep learning-based. For a hand-crafted features-based approach, the most commonly used features are color-based information in addition to traditional texture approaches [12, 15, 20-23]. The color-based information has been common because there are significant differences between normal and abnormal cases of eardrums. The deep learning-based approach is also used more than the texture-based approach because it is typically more accurate [4, 24]. One study has used both a hand-crafted and deep learning-based approach to classify otoscopy images [7].

However, prior work in CAD for OM abnormalities has only been applied to single ear (i.e., either right or left) TM images. For example, Lee et al. proposed a convolutional neural network (CNN)-based approach that detects the ear's side, but this information was not used to classify paired images (right and left ears) together [25]. However, physicians typically examine both ears during a physical exam before making a diagnosis.

Therefore, systems and methods are desired that overcome challenges in the art, some of which are described above. In particular, there is a need for a timely and accurate method and system to analyze otoscopy images in order to properly identify and classify any of a multitude of ear pathologies.

SUMMARY

Herein we disclose and describe automated otoscopy image analysis systems and methods that compare a set of images (images from both a right ear and a left ear). The disclosed systems and methods use deep learning and color-based features to classify a pair of TM images. Image classifications may include, for example, 'normal-normal,' 'normal-abnormal,' 'abnormal-normal,' or 'abnormal-abnormal.' To extract deep learning-based features, a lookup table may be created and used. Image pre-processing steps are used for creating the lookup table. The lookup table values of the paired images were analyzed according to their labels to determine the association between right and left ear values. Additionally, the contribution of color-based features may be used to better the classification accuracy.

Disclosed and described herein are methods, systems and computer program products for classifying tympanic membrane pathologies from images of both a left and a right tympanic membrane of a subject. Methods, systems and computer program product are described and disclosed for capturing one or more images of each of a left tympanic membrane and one or more images of a right tympanic membrane of a subject using an image capture device; performing preprocessing and data augmentation on the captured one or more images of the left tympanic membrane and the right tympanic membrane of the subject to create a composite image of the right tympanic membrane and a composite image of the corresponding left tympanic membrane of the subject to form a pair of eardrum images for the subject; extracting features from the pair of eardrum images; forming a feature vector for the pair of eardrum images using the extracted features; and classifying pathologies of the pair of eardrum images.

Additional advantages will be set forth in part in the description, which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and, together with the description, serve to explain the principles of the methods and systems.

DETAILED DESCRIPTION

Figure 1:
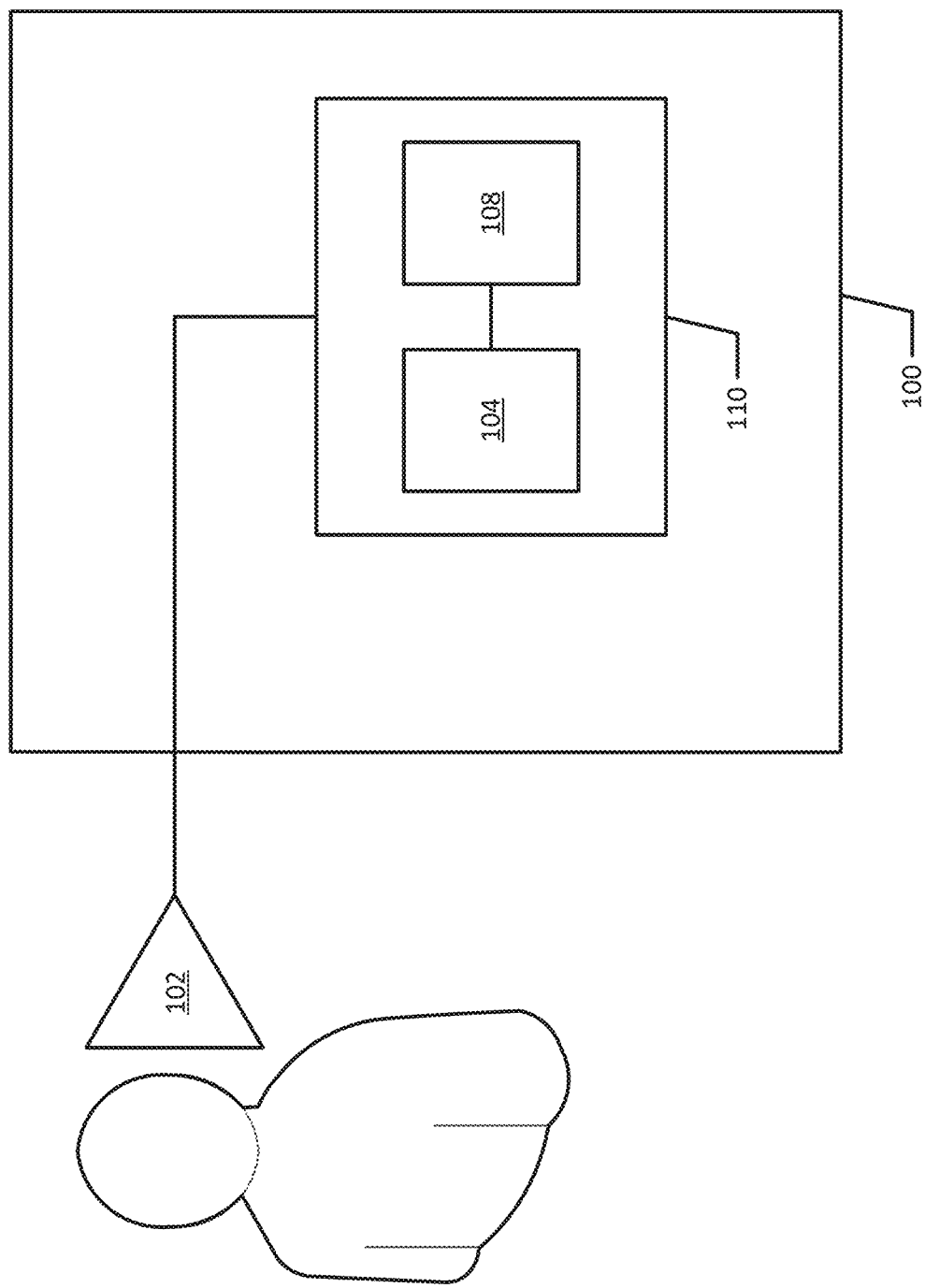
FIG. 1 illustrates an exemplary overview system for classifying eardrum pathologies from images from both, a right eardrum and a left eardrum of a single subject.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application, including, but not limited to, steps in disclosed methods. Thus, if there are a variety of additional steps that can be performed, it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized, including hard disks, CD-ROMs, optical storage devices, or magnetic storage devices.

Embodiments of the methods and systems are described below with reference to block diagrams and flowchart illustrations of methods, systems, apparatuses, and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present methods and systems may be understood more readily by reference to the following detailed description of preferred embodiments and the Examples included therein and to the Figures and their previous and following description.

FIG. 1 illustrates an exemplary overview system for classifying ear pathologies from sets of images of both a left and a right ear of a person. As shown in FIG. 1, one embodiment of the system 100 comprises an image capture mechanism 102. In one aspect, the image capture mechanism 102 can be a camera. More specifically, the image capture mechanism 102 may be a digital otoscope. The image capture mechanism 102 can take still and/or video images of each ear. Generally, the image capture mechanism 102 is a digital camera, but can be an analog device equipped with or in communication with an appropriate analog/digital converter. The image capture mechanism 102 may also be a webcam, scanner, recorder, or any other device capable of capturing a still image or a video. In some instances, the system may comprise two image capture mechanisms 102 for capturing images of each ear either simultaneously or in sequence.

As shown in FIG. 1, the image capture mechanism 102 is in direct communication with a computing device 110 through, for example, a network (wired (including fiber optic)), wireless or a combination of wired and wireless) or a direct-connect cable (e.g., using a universal serial bus (USB) connection, IEEE 1394 "Firewire" connections, and the like). In other aspects, the image capture mechanism 102 can be located remotely from the computing device 110, but capable of capturing images and storing them on a memory device such that the images can be downloaded or transferred to the computing device 110 using, for example, a portable memory device and the like. In one aspect, the computing device 110 and the image capture mechanism 102 can comprise or be a part of a device such as a smart device, smart phone, tablet, laptop computer or any other fixed or mobile computing device.

In a basic configuration, the computing device 110 can be comprised of a processor 104 and a memory 108. The processor 104 can execute computer-readable instructions that are stored in the memory 108. Moreover, images captured by the image capture device 102, whether still images or video, can be stored in the memory 108 and processed by the processor 104 using computer-readable instructions stored in the memory 108.

The processor 104 is in communication with the image capture device 102 and the memory 108. The processor 104 can execute computer-readable instructions stored on the memory 108 to capture, using the image capture device 102, a set of images of both, the left ear and the right ear of a subject. In one aspect, the captured images can include a set of images of a left eardrum and a right eardrum of a subject.

The processor 104 can further execute computer-readable instructions stored on the memory 108 to capture, using the image capture device 102, one or more sets of digital images and classify ear pathologies from the one or more sets.

Figure 2A:
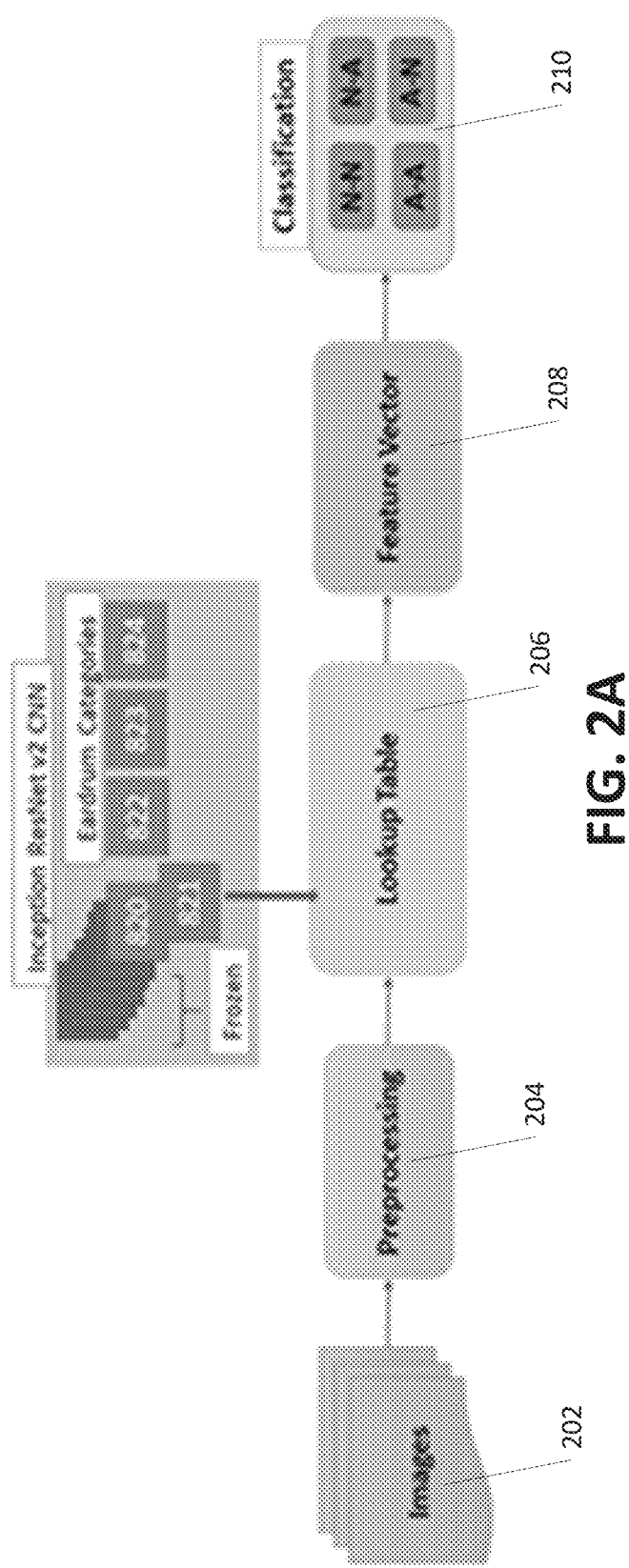
FIG. 2A illustrates modules that comprise an embodiment of an approach to classify ear pathologies based on using the right and left eardrum otoscopy images for automated otoscopy image analysis.

FIG. 2A illustrates modules that comprise an embodiment of an approach to classify ear pathologies based on using right and left eardrum otoscopy images for automated otoscopy image analysis. These modules may comprise software, which can be executed by the processor 104. These modules comprise capturing image sets 202; preprocessing and data augmentation 204; feature extraction to generate a lookup table 206; feature vector formation for a pair of eardrum images 208; and classification for the pairs 210. Each of these modules are described in greater detail herein. The image acquisition process has been described above with reference to FIG. 1.

An otoscope such as an HD video otoscope (e.g. JEDMED Horus+ HD Video Otoscope, St. Louis, MO) can be used to capture one or image sets or videos of pairs of eardrums (left ear and right ear of the same subject). Although the higher resolution of collected HD images allows identification of some of the abnormalities, some of the design issues of this product may cause challenges for autonomous recognition. In the preprocessing module 202, these challenges are reduced and the images are prepared for computation of their features.

The acquisition of adequate images can be a challenging task because of visual obstruction (e.g., wax, hair, etc.), poor illumination, a small field of view, black margins around the images, time/text stamps on the image, and the like. If the patient is a child, there may also be the problem of being able to capture a good still image while the patient is uncooperative. To solve these challenges, a short video (around 3-5 seconds) of each ear canal of the subject is captured. Then, software, executing the algorithm shown in FIG. 2B, analyzes video frames of the eardrum and creates a new mosaicked image.

Figure 2B:
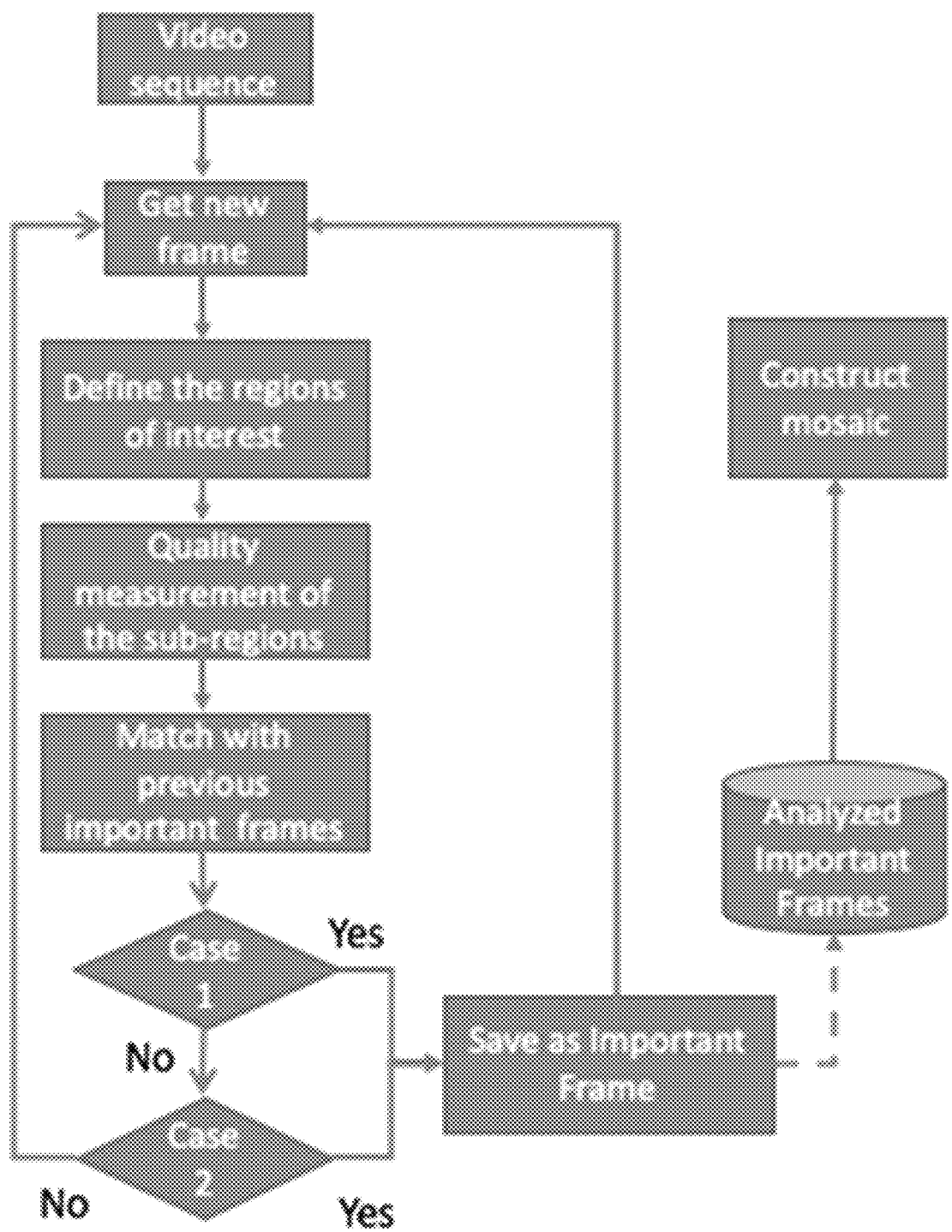
FIG. 2B illustrates a flow diagram for an exemplary composite image generation method where Case 1 occurs when a new frame includes new regions of interest that are not covered previously by another important frame, and Case 2 occurs if the region which is already covered by a previous important frame has a higher quality in this new frame.

For each new frame in the video sequence, the mosaic image creation algorithm as described in FIG. 2B determines the regions of interest which are free of obstruction (e.g., wax, hair, dark margins, text, etc.). Each of these regions is divided into subsections, and the image quality in each section is evaluated in terms of being in-focus, having adequate contrast and illumination. If the frame includes the part of the eardrum that is not included in the previous frames, or includes an already included part of the eardrum but with higher quality (in terms of focus, contrast and illumination), then this frame is labeled as an "important frame" or otherwise identified. Finally, the new method constructs the mosaic image by considering the regions of interest in all the "important frames" in the video sequence.

The frames may include different amounts of visual obstruction (e.g., wax, hair, glare, text, dark margins, etc.) and/or quality of illumination. As described herein, the method includes constructing composite obstruction-free images with excellent illumination. Therefore, the algorithm detects obstructions (wax, glare, hair, text, dark margins—see below) and out-of-focus regions during the composite image generation. To do that, the algorithm compares each new frame with the previous frames and updates the new image using the regions that are more in-focus and well-illuminated. To decide on in-focus and illumination quality, an image entropy is computed, and the frame with the highest entropy is selected.

Regarding wax detection, one of the typical characteristics of cerumen is its yellow color. Therefore, yellow regions are identified by using thresholding in CMYK color space. After these potential cerumen regions are detected as those regions with the highest "Y" values in the CMYK space, the mean and standard variation of the gradient magnitude of the intensities (i.e. "Y" values) of these cerumen regions are computed. These features are input to the FSG classifier to detect wax regions.

Glare is caused by the reflection of light from the otoscope on the surface of the tympanic membrane. Glare may be a problem for the calculation of some of the features (e.g., the mean color value of tympanic membrane). On the other hand, the cone of light, an important clinical diagnostic clue, can be inadvertently considered as glare by the glare detection algorithm and removed. In order to correctly extract the features, the disclosed method includes calculating the histogram of the intensity values and finds the peak corresponding to the highest intensity value in the histogram. That peak corresponds to the glare and cone of lights. To differentiate between the glare and cone of lights, area thresholding is applied (where glare(s) is larger than the cone of light(s)).

Hair detection includes detecting thin linear structures by using a line segment detector such as that described in R. G. von Gioi, J. Jakubowicz, J.-M. Morel, and G. Randall, "LSD: A fast line segment detector with a false detection control," IEEE transactions on pattern analysis and machine intelligence, vol. 32, pp. 722-732, 2010, which is incorporated by reference. Each hair strand is represented by two lines (both edges of the hair), approximately parallel to each other and the lines are close to each other. So, each approximately parallel line pair with a short distance is considered a hair candidate. The image texture is calculated between these parallel lines, and those with small textural variation are marked as hair.

In some instances, after the regions of interest are extracted, these regions are divided into 64×64 pixel blocks. For each block, the standard deviation, gray level co-occurrence matrix, contrast, and the mean intensity value are calculated. These values are weighted to calculate the tile quality. The weights may be determined manually or automatically.

To register two frames, points of interest are automatically extracted and the feature vectors for these points are matched. To extract points of interest, the performance of three state-of-the-art approaches is compared (see H. Bay, T. Tuytelaars, and L. Van Gool, "Surf: Speeded up robust features," Computer vision—ECCV 2006, pp. 404-417, 2006; D. G. Lowe, "Distinctive image features from scale-invariant keypoints," International journal of computer vision, vol. 60, pp. 91-110, 2004; and E. Rublee, V. Rabaud, K. Konolige, and G. Bradski, "ORB: An efficient alternative to SIFT or SURF," in Computer Vision (ICCV), 2011 IEEE International Conference on, 2011, pp. 2564-2571, each of which is fully incorporated by reference.). In order to identify the matched points, the approach computes the distance between all possible pairs of detected features in two frames. The approach estimates the initial Homograph matrix with Random Sample Consensus (RANSAC) (see M. A. Fischler and R. C. Bolles, "Random sample consensus: a paradigm for model fitting with applications to image analysis and automated cartography," *Communications of the ACM*, vol. 24, pp. 381-395, 1981, which is also incorporated by reference).

Each frame is identified as an "important frame" or not according to two criteria: (1) If the new frame includes new regions of interest which are not covered previously by another important frame; or (2), if the region which is already covered by a previous important frame has a higher quality in this new frame. A composite image can then be created by stitching. The disclosed method uses "important frames" during the composite image construction. The algorithm selects the most suitable "important frames" for sub-parts of the eardrum and uses a multi-band blending (pyramid blending) method, which ensures smooth transitions between images despite illumination differences, while preserving high-frequency details.

As noted herein, preprocessing may also comprise embedded text removal. In many instances, images captured by an otoscope embeds the date and time information in the image for clinical purposes. In preprocessing, it may be desired to remove this embedded date and time information. In order to detect the embedded text, intensity ratios of the different bands and gradient information are used together. Due to the prior information about the possible location and color range of the text, this solution allows detection of text characters with a high recall rate. The detected text pixels are used to create a guidance field and the magnitude of the gradient is set to zero for these pixels. Finally, the overlaid text is seamlessly concealed.

The preprocessing module 202 may further comprise region of interest (ROI) detection. The ROI, which includes the eardrum, can be in any location in the whole image due to the physical characteristics of the tip of the image capture device (e.g., otoscope) used. Also, the tip characteristic may cause some reflection problems at the boundary of the tip in the image. In order to solve this problem, the algorithm clusters all of the pixels according to their intensity values and then selects the background regions by considering the majority of pixels on the image boundary. After the background pixels are detected, the possible foreground pixels are fitted to an ellipse by using linear least square with Bookstein constraint. Finally, a morphological erosion operation is applied to get rid of possible glare artifacts around the tip.

The preprocessing module 202 may also comprise glare detection and removal. One of the most critical artifacts in images is glare, caused by the reflection of light from the image capture device (e.g., otoscope, including a high-resolution digital otoscope) on the surface of the tympanic membrane. Glare may be a challenge for the calculation of some of the features (e.g., the mean color value of tympanic membrane). On the other hand, the cone of light, an important clinical diagnostic clue, can be inadvertently considered as glare by the glare detection algorithm and removed. In order to correctly extract the features, a histogram of the intensity values is calculated and finds the related peak in the histogram that corresponds to the glare. After the glare detection, the algorithm creates a modified copy of the image where detected regions of glare are seamlessly blended to the rest of the image.

One step is obtaining a dataset to train an artificial intelligence (AI) network to recognize an image of a normal ear and an image of an abnormal ear. Those various datasets may be used for training purposes, in this non-limiting instance all the images used were captured from adult and pediatric patients at primary care clinics and Ear, Nose, and Throat (ENT) facilities of the Ohio State University (OSU) and Nationwide Children's Hospital (NCH) in Columbus, Ohio, US with the IRB approval (Study Number: 2016H0011). Additionally, conforming to the rules set by the Ohio State University Institutional Review Board, all the samples were fully anonymized while creating the experimental dataset.

A total of 150-pair (i.e., 300 individual) eardrum images were used to train and test the system. Each pair comprises the right and left ear images of the same person captured in the same visit. The number of images for each category (normal-abnormal) is shown in Table 1. In this example, only two categories of abnormality: effusion (fluid) of the middle ear and tympanostomy tube were included because there was not a sufficient number of images in other categories to train and test the classifiers properly. However, the system may be trained using images of any time of ear abnormality that can be determined from visual information. Again, in this non-limiting example, because of the limited number of abnormalities captured in the dataset, the problem of normal-abnormal pair classification as opposed to classifying the pairs according to the type of abnormality separately. In addition to the number of pair images, 137 single images (83-Abnormal, 54-Normal) were used to validate the developed system's deep learning part while extracting the lookup table features.

TABLE 1

The number of images for each class of eardrum types. Both right and left eardrum images have the same diagnosis, and right and left different category image numbers in the dataset

| Category | Number of Single Images | Number of the same Category Pair Images | Number of the Right Images | Number of the Left Images |
| --- | --- | --- | --- | --- |
| Normal | 168 | 71 | 14 | 12 |
| Abnormal (Effusion-Tube) | 132 | 53 | 12 | 14 |
| Total | 300 | 124 | 26 | 26 |

Figures 3A, 3B, 3C, 3D, 3E, 3F:
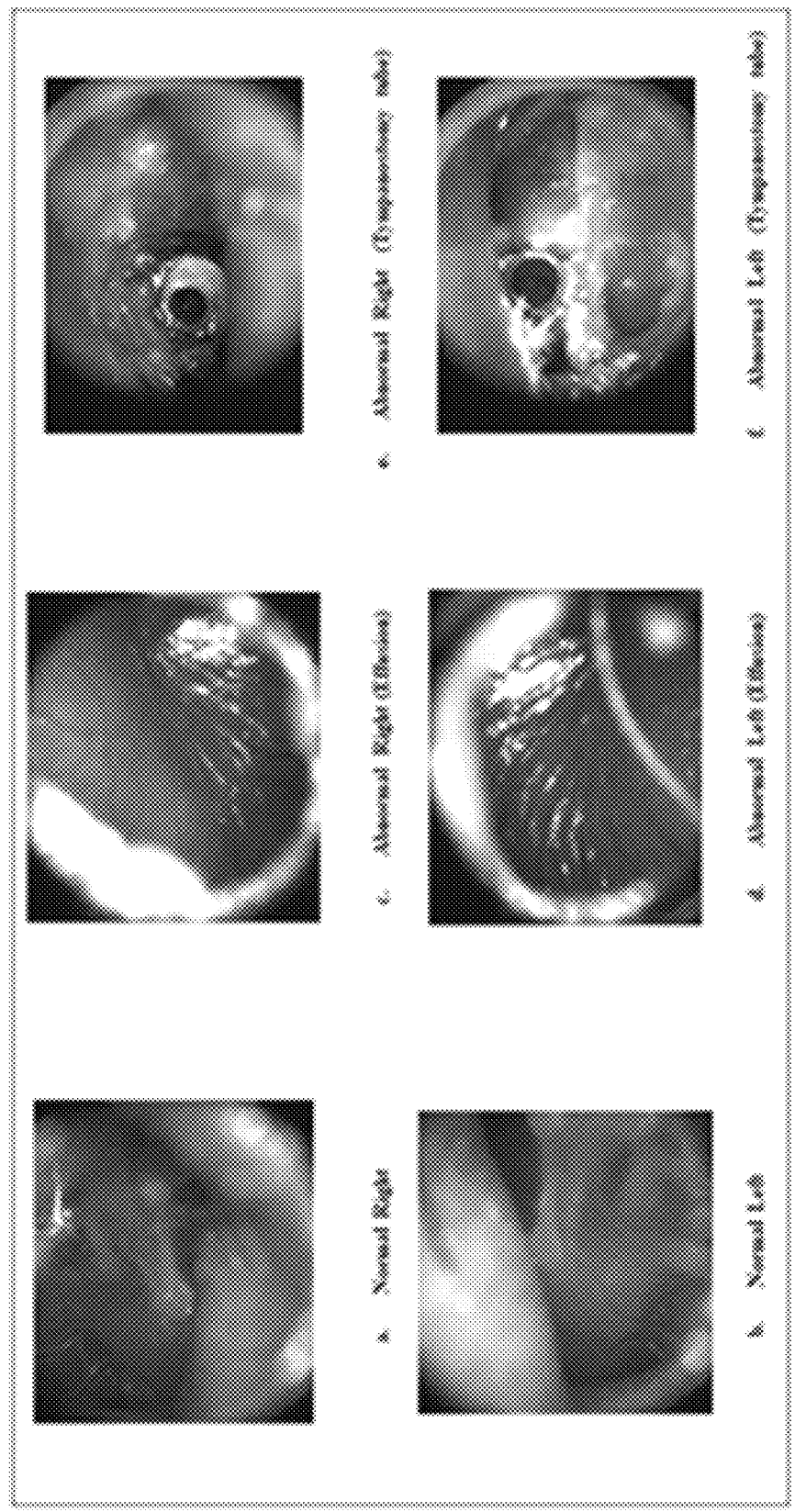
FIGS. 3A-3F show paired examples from normal, abnormal with effusion, and abnormal with tympanostomy tube categories, demonstrating the variability among the images in different categories.

FIGS. 3A-3F show paired examples from normal, abnormal with effusion, and abnormal with tympanostomy tube categories, demonstrating the variability among the images in different categories. Images from some categories are difficult to distinguish from the others for an untrained person. In many cases, the similarities between the right and left ear are not obvious. As can be seen in FIGS. 3e and 3f, the tympanostomy tube abnormality appears differently for the same patient.

Because increasing the number of paired images was needed for training and validation. all the paired image datasets were used. The database contained images captured in the JPEG format, those other image formats may be used. Additionally, individual images were selected from the frames of otoscopy video clips. Both single images and video frames were the same size (1440 by 1080 pixels) and resolution, though other sizes and resolutions may be used. Some of the images in the video frames were unfocused, contained large amounts of wax, or did not have the proper illumination. Therefore, the best single images and frames were manually selected to form the appropriate pair of images.

It is to be appreciated that once the system is trained and validated using the dataset of images, then the system can receive and analyze images captured of a subject's ears, as described with respect to FIG. 1, above.

Referring back to FIG. 2A, a second module is data augmentation and preprocessing 204. A data augmentation approach was used to increase the number and diversity of images for transfer learning. The augmentation approached included reflecting images both horizontally and vertically, scaling images in the range of 0.7 to 2, rotating images randomly, shearing images both horizontally and vertically within a range of 0 to 45 degrees, and translating them within a pixel range from −30 to 30 pixels in both horizontal and vertical directions. Data augmentation may be applied to images used for training and validation, as well as images captured for analysis.

To extract features from these images, regions of interest (RoI) were extracted in the preprocessing step, which is described above.

Forming Feature Vector

To classify the eardrum pairs as normal or abnormal, the feature extraction and lookup table module 206 was completed in two steps: transfer learning-based lookup table feature extraction and handcrafted feature extraction. The transfer learning-based lookup table features are the same as in S. Camalan et al., "OtoMatch: Content-based eardrum image retrieval using deep learning," Plos one, vol. 15, no. 5, p. e0232776, 2020, which is incorporated by reference, for the eardrum image retrieval system. Herein, lookup table feature extraction and handcrafted feature extraction are integrated into the pairwise classification system, as described below. The handcrafted features included registration error, histogram, and statistical measurements of the a* and b* components of the L*a*b* color space.

Transfer Learning Based Feature Extraction

Deep learning can be used to classify eardrum abnormalities. The method may include at least one of the following networks: (1) an existing network model, i.e. ResNet-50[8], Inception v3 [9], or Inception-Resnet [10] which is already trained on a different dataset (like imagenet), is used for transfer learning (see K. He, X. Zhang, S. Ren, and J. Sun, "Deep residual learning for image recognition," in Proceedings of the IEEE Conference on Computer Vision and Pattern Recognition, 2016, pp. 770-778; C. Szegedy, V. Vanhoucke, S. Ioffe, J. Shlens, and Z. Wojna, "Rethinking the inception architecture for computer vision," in Proceedings of the IEEE Conference on Computer Vision and Pattern Recognition, 2016, pp. 2818-2826; and C. Szegedy, S. Ioffe, V. Vanhoucke, and A. Alemi, "Inception-v4, inception-resnet and the impact of residual connections on learning," arXiv preprint arXiv:1602.07261, 2016, each of which are fully incorporated by reference).

In one instance, an Inception-ResNet-V2 Convolutional Neural Network (CNN) is trained with otoscope images from the dataset. After training the network, the resulting features were subjected to pooling that mapped each image into a vector of 1,536 features. The connected layer's output was relied upon, which produced 1×3 vectors for each training and test image, where three represents the number of image categories in our database: normal, effusion, tympanostomy tube. The features formed a 1536×1 vector at the output of the average pooling layer. Therefore, the weights were a 1536×3 matrix of the fully connected layer. When the transpose of the feature vector was multiplied by the weight vector, it produced a 1×3 vector, which was established for each of the training set of images. When these vectors were turned to rows of a matrix (size of the number of training images×3), this comprises the lookup table.

This procedure was applied to a pair of eardrum images for normal/abnormal feature extraction. The number of categories was two (i.e., normal, abnormal), and the weights constitute a 1536×2 matrix of the fully connected layer. The generated lookup table is a vector of length N×2, where N is the number of training images. Also, test images have a 1×2 vector after multiplying them by weights. For each pair of the eardrum images, these lookup values are calculated, and a new feature vector is formed using these values.

The steps to create a lookup table from transfer learning can be generalized as follows:

Form a feature vector $f_i$ as the average pooling layer output for each image, i. Its size is (F×1) (F=1536 in this case).

Let w, of size (F×C), be the weights of the fully connected layer, where C is the number of training classes (C=2 in this case because of two categories: 'normal' and 'abnormal').

The lookup table values $l_i$ for one image, i, can be calculated as $l_i = l_i = f_i^T \times w$ and its size is (1×C).

If N is the number of images in the dataset (both for training and testing), the lookup table $L_T$ is a matrix calculated as concatenation of the lookup table values $l_i$ for each image, i and with size N×C (300×2 for this case).

The lookup table values of the right eardrum image are $R_1$ and $R_2$, and of the left eardrum image are $L_1$ and $L_2$. Their ratio ($R_1/L_1$, $R_2/L_2$), summation ($R_1+L_1$, $R_2+L_2$), and difference ($R_1-L_1$, $R_2-L_2$) are also concatenated to form a feature vector. This new vector, which contains both eardrum pairs' features, enables classification of the pair together by combining the derivative of lookup table values for a pair of eardrum images.

Handcrafted Feature Extraction

In addition to the lookup table-based features, handcrafted features were also used, which captured the registration errors between pair eardrum images. The registration is used to match and compare two or more images obtained at different times from different sensors or different viewpoints to find the best transformation that portrays good spatial correspondence among them [26, 27]. Image registration is frequently used in medicine to align images from different medical modalities for diagnosis, treatment monitoring, surgery simulation, radiation therapy, assisted/guided surgery, and image subtraction for contrast-enhanced images [28-31]. As described herein, image registration is used to calculate the error between the pair of eardrum images and used as a feature to classify pairs together.

Eardrum image registration is challenging even for normal cases because the malleus is positioned differently in the eardrum images of the right and left sides of the same person. Furthermore, the pair images are rarely symmetric, nor are they obtained from the same perspective when captured with an otoscope. For diseased eardrums, registration is more challenging than that for normal cases because some diseases (e.g., effusion) lead to changes in the eardrum shape and cannot be easily detected with 2D images.

Herein, both rigid and non-rigid registration is used. For both types of registration, there should be moving and target images; moving (source) images transform spatially to align with the target (fixed, sensed) image. Rigid registration [32] includes translation, scaling, and rotation of the moving image to the target image, and non-rigid matching is done using the demons method [33], which transforms the points depending on Maxwell's demons and match the deformed parts of the image. The basis of demon registration forces finds small deformations in temporal image sequences by calculating the optical flow equations. Therefore, the displacement is estimated by the Thirion method [33] for corresponding match points. Because the demons equation approximates the local displacement in each iteration, Gaussian smoothing is used for displacement for regularization.

Before registration, each image is converted from color (RGB) to a gray-scale image, and the registration is applied to the gray-scale images. For rigid registration, mutual information is used as the similarity metric. For optimization, a one-plus-one evolutionary optimization algorithm [34, 35], which iterates the set of parameters to produce the best possible registration, is used with the initial radius's parameter is 0.009, epsilon is 1.5×10−4, the growing factor is 1.01, and a maximum of 300 iterations. After rigid registration, non-rigid demon algorithm image registration [36] with a single modality parameter is applied to a rigid registered image.

The mean square error between fixed image and registration images is computed as the difference of corresponding pixels and taking the mean square of them and used as a similarity metric between fixed and moving images. One of the mean square errors is computed after rigid registration, and another one is after non-rigid registration. These two mean square errors concatenated to feature vector starts with lookup table based values.

Figure 4:
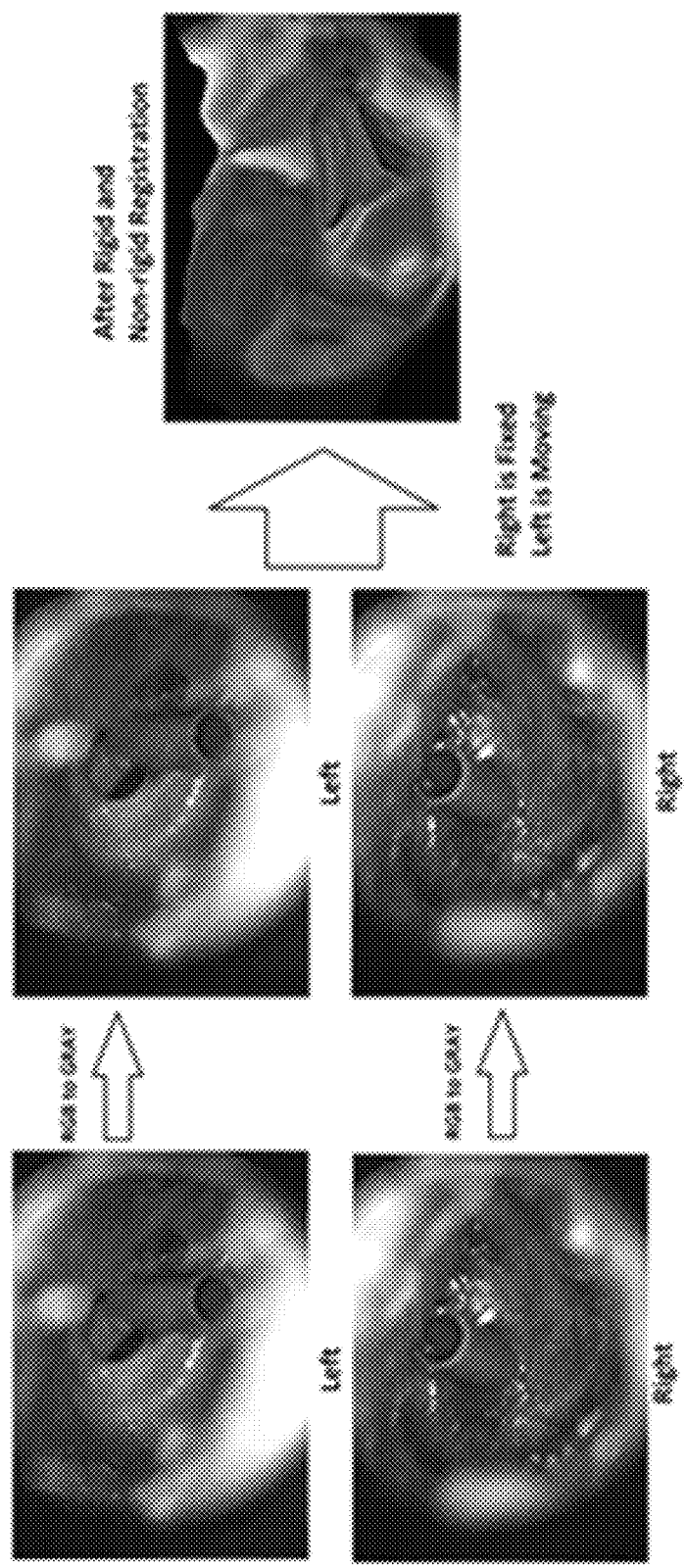
FIG. 4 illustrates right and left eardrum image with tympanostomy tube diagnosis.

FIG. 4 illustrates right and left eardrum image with tympanostomy tube diagnosis. The right image is considered fixed, and the left image is considered moving to match two images. The rightmost image shows the after registration of rigid and non-rigid demons algorithm.

a* and b* components of the L*a*b* color space of each pair of eardrum images to extract color-based features are used to classify the pairs accurately. The L*a*b* color space is the uniform color space with equal distances on the x, y chromaticity diagram that corresponds to equal perceived color difference. In this color space, L* indicates lightness, and a* and b* are the chromaticity coordinates where +a* is the red direction, −a* is the green direction, +b* is the yellow direction, and −b* is the blue direction. The RGB color images are converted to the L*a*b* color space, and the histogram and statistical measurements of the a* and b* bands are calculated. The histogram of color bands is divided into ten bins, and the number of each bin is concatenated to the feature vector for each pair of images. There are 40 histogram values, which come from two images (right and left images) and two bands (a* and b* bands) for each ear pair. In addition to the histogram values, statistical measurements of mean, standard deviation, skewness, and kurtosis of each band of pairs. A total of 16 features come from these four statistical measurements. A graphical summary of the new feature vector formation is shown in FIG. 5.

Figure 5:
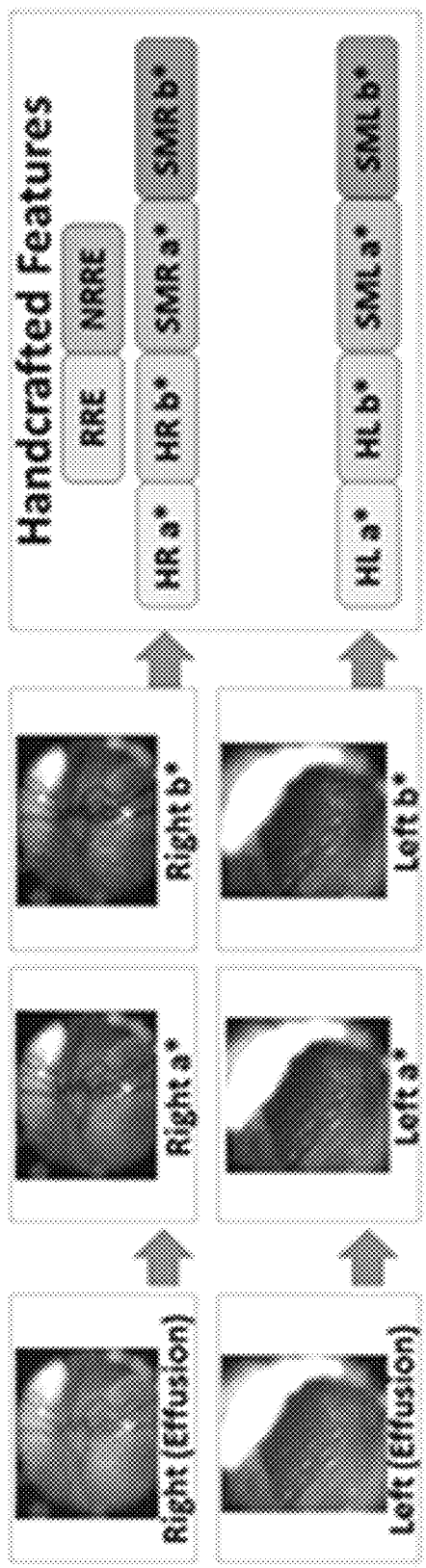
FIG. 5 illustrates the creation of a feature vector structure for a pair of eardrum images.

FIG. 5 illustrates creation of a feature vector structure for a pair of eardrum images. Rigid and Non-Rigid registration errors were calculated for a pair of eardrums. RGB pair images are converted to the L*a*b* color space, and a* and b* components are used for creating color histograms and calculating statistical measurements. All features are concatenated to form a handcrafted feature vector, where RRE: Rigid Registration Error, NRRE: Non-Rigid Registration Error, HR a*: Histogram of Right a*, HR b*: Histogram of Right b*, HL a*: Histogram of Left a*, HL b*: Histogram of Left b*, SMR a*: Statistical Measurements of Right a*, SMR b*: Statistical Measurements of Right b*, SML a*: Statistical Measurements of Left a*, and SML b*: Statistical Measurements of Left b*.

Classification

After the feature vector of the pair (right and left) eardrum images is formed by concatenating the lookup table values with handcrafted features, these are classified. To classify a pair of images together, all the features are collected in one vector for each pair. Thus, the difference between classifying single images and classifying pairs as 'Normal-Normal,' (N-N) 'Abnormal-Abnormal,' (A-A) 'Normal-Abnormal,' (N-A) and 'Abnormal-Normal' (A-N) can be analyzed. Single image classification results were obtained after training the Inception ResNet-v2 pre-trained network by changing the last three layers according to 'Normal/Abnormal' classes of eardrum images. For the paired image classification, a newly created feature vector is used in the Tree Bagger algorithm.

Tree Bagger algorithm is the ensemble model of bootstrap aggregated decision trees. Multiple decision trees constitute resampling training data with replacement again and again and voting the trees for majority prediction [37]. These decision trees are the classification trees whose leaves represent class labels; branches represent conjunctions of features which convey to these class labels. In the disclosed, the leaves are the 'Normal' and 'Abnormal' class labels, and the branches are the conjunction of the feature vector. The out-of-bag (OOB) error method [38] was utilized to measure the prediction error of boosted decision trees models to sub-sample data to train the method. The OOB error is measured by excluding a sub-sample from training data and calculating the mean prediction error in the bootstrap sample [39]. Subsampling improves the prediction performance by evaluating predictions on observations that are not used in building the tree (defined out-of-bag).

This study modeled the decision tree using the TreeBagger supervised machine learning function in Matlab 2019B software. Selected trees, where the observation is out of the bag, compose the class posterior probabilities' weighted mean. So, the predicted class is the largest weighted mean of a corresponding class. This is also designed to improve the model's stability and accuracy by reducing the variance without raising the bias. The optimal number of trees decided according to the out-of-bag error changes with the accumulation of trees. In our study, the number of classes (normal and abnormal) and the number of observations (150 pair eardrum image) limit the number of decision trees, which is empirically selected as five.

Figure 6:
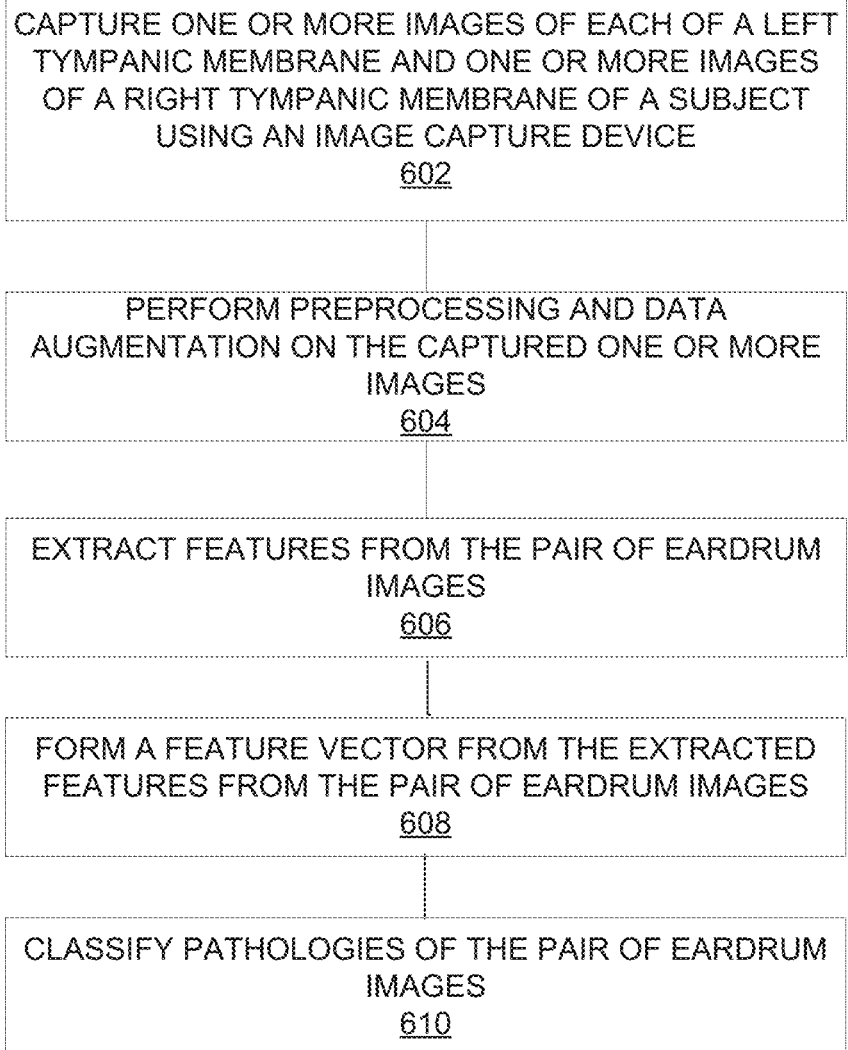
FIG. 6 is a flowchart that illustrates an exemplary method of classifying eardrum pathologies using the right and left eardrum otoscopy images of a subject.

FIG. 6 is a flowchart that illustrates an exemplary method of classifying ear pathologies from images of both a left and a right tympanic membrane of a subject. In one embodiment, the method comprises 602 capturing one or more images of each of a left tympanic membrane and one or more images of a right tympanic membrane of a subject using an image capture device. In various instances, image capture device captures one or more still images of each of the tympanic membranes or captures a video of each of the tympanic membranes. For example, the image capture device may comprise a high-resolution otoscope or a digital video-otoscopes. At 604, preprocessing and data augmentation is performed on the captured one or more images of the left tympanic membrane and the right tympanic membrane of the subject to create a composite image of the right tympanic membrane and a composite image of the corresponding left tympanic membrane of the subject to form a pair of eardrum images for the subject. Preprocessing may include one or more of reducing sensor based problems, selecting a region of interest in the one or more images, detecting glare effects (light reflections), wax, hair, dark margins, and text and creating a copy of the one or more images where the glare effects, wax, hair, dark margins and text are reduced or removed from the composite image of the right tympanic membrane and the composite image of the corresponding left tympanic membrane of the subject. Data augmentation may include reflecting each of the one or more images both horizontally and vertically, scaling each of the one or more images in the range of 0.7 to 2, rotating each of the one or more images randomly, shearing each of the one or more images both horizontally and vertically within a range of 0 to 45 degrees, and translating them within a pixel range from −30 to 30 pixels in both horizontal and vertical directions.

At 606, features from the pair of eardrum images are extracted. At 608, a feature vector is formed for the pair of eardrum images using the extracted features. The extracted features are concatenated to form a single feature vector. The feature vector has two parts, a first part comprised of lookup table-based values created by using deep learning techniques, and a second part comprised of handcrafted features created by recording registration errors between paired eardrums, color-based features such as histogram of a* and b* component of the L*a*b* color space, and statistical measurements of these color channels. The deep learning techniques may include transfer-based learning. The transfer-based learning may comprise retraining deep learning networks including Inception V3 or ResNet. At 610, pathologies of the pair of eardrum images are classified. In some instances, classifying pathologies of the pair of eardrum images comprises classifying the single feature vector by a tree bagger classifier. Generally, classifying pathologies of the pair of eardrum images comprises classifying each eardrum as normal or abnormal. The abnormalities may include one or more of acute otitis media (AOM), middle ear effusion (non-infected fluid), cholesteatoma (a common destructive skin cyst in the ear), eardrum perforation, and eardrum retraction vs normal.

The system has been described above as comprised of units. One skilled in the art will appreciate that this is a functional description and that the respective functions can be performed by software, hardware, or a combination of software and hardware. A unit can be software, hardware, or a combination of software and hardware. The units can comprise software for discriminating tissue of a specimen. In one exemplary aspect, the units can comprise a computing device that comprises a processor 721 as illustrated in FIG. 7 and described below.

Figure 7:
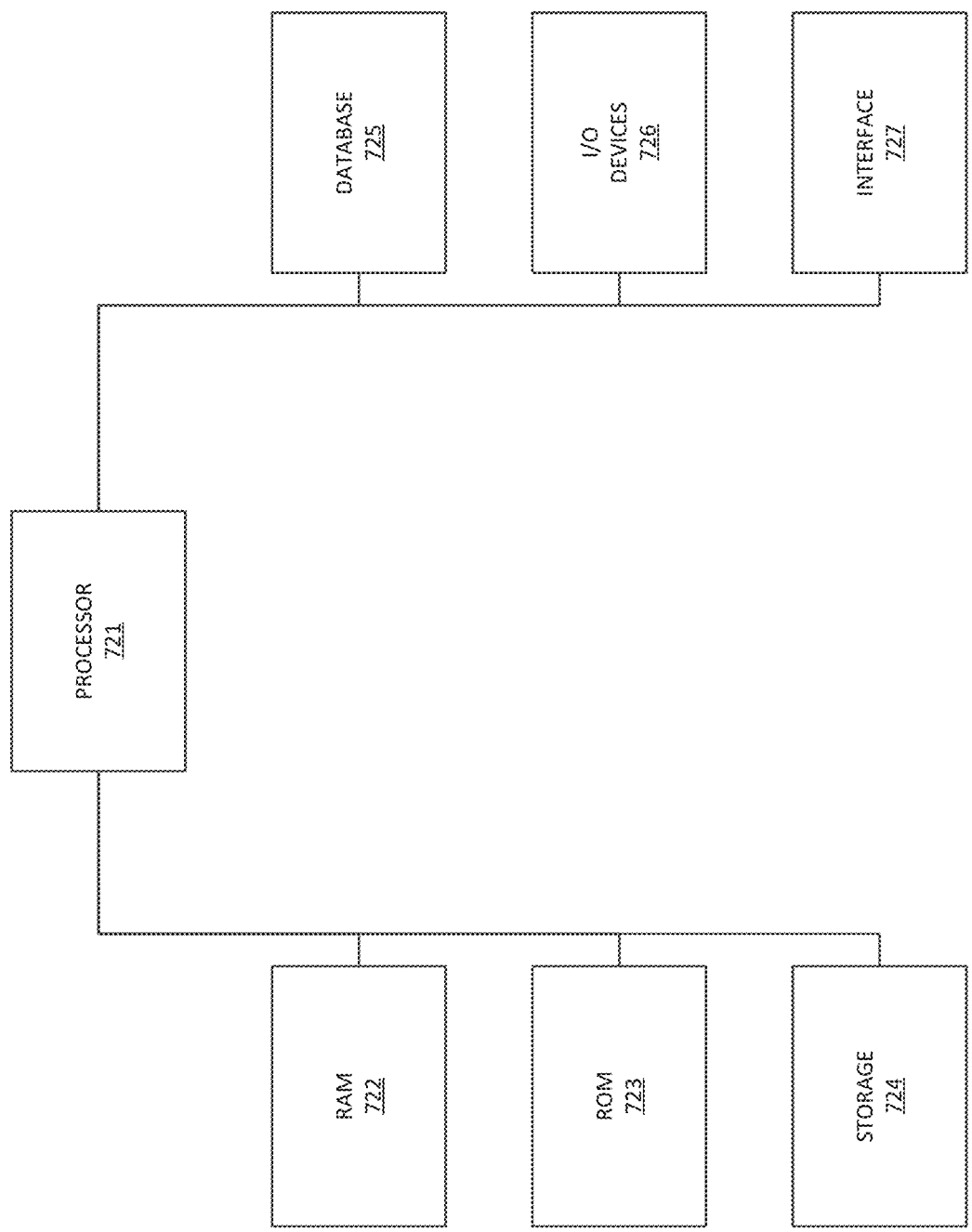
FIG. 7 illustrates an exemplary computer that can be used for classifying tympanic membrane pathologies using the right and left eardrum otoscopy images of a subject.

FIG. 7 illustrates an exemplary computer that can be used for classifying tympanic membrane pathologies from images. As used herein, "computer" may include a plurality of computers. The computers may include one or more hardware components such as, for example, a processor 721, a random access memory (RAM) module 722, a read-only memory (ROM) module 723, a storage 724, a database 725, one or more input/output (I/O) devices 726, and an interface 727. Alternatively and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 824 may include a software partition associated with one or more other hardware components. It is understood that the components listed above are exemplary only and not intended to be limiting.

Processor 721 may include one or more processors, each configured to execute instructions and process data to perform one or more functions associated with a computer for classifying pathologies of an eardrum based upon one or more images of the eardrum. Processor 721 may be communicatively coupled to RAM 722, ROM 723, storage 724, database 725, I/O devices 726, and interface 727. Processor 721 may be configured to execute sequences of computer program instructions to perform various processes. The computer program instructions may be loaded into RAM 722 for execution by processor 721.

RAM 722 and ROM 723 may each include one or more devices for storing information associated with operation of processor 721. For example, ROM 723 may include a memory device configured to access and store information associated with the computer, including information for identifying, initializing, and monitoring the operation of one or more components and subsystems. RAM 722 may include a memory device for storing data associated with one or more operations of processor 721. For example, ROM 723 may load instructions into RAM 722 for execution by processor 721.

Storage 724 may include any type of mass storage device configured to store information that processor 721 may need to perform processes consistent with the disclosed embodiments. For example, storage 724 may include one or more magnetic and/or optical disk devices, such as hard drives, CD-ROMs, DVD-ROMs, or any other type of mass media device.

Database 725 may include one or more software and/or hardware components that cooperate to store, organize, sort, filter, and/or arrange data used by the computer and/or processor 721. For example, database 725 may store digital images of both left and right tympanic membranes of subjects, along with computer-executable instructions for performing preprocessing and data augmentation on the captured one or more images of the left tympanic membrane and the right tympanic membrane of the subject to create a composite image of the right tympanic membrane and a composite image of the corresponding left tympanic membrane of the subject to form a pair of eardrum images for the subject; extracting features from the pair of eardrum images; forming a feature vector for the pair of eardrum images using the extracted features; and classifying pathologies of the pair of eardrum images. It is contemplated that database 725 may store additional and/or different information than that listed above.

I/O devices 726 may include one or more components configured to communicate information with a user associated with computer. For example, I/O devices may include a console with an integrated keyboard and mouse to allow a user to maintain a database of digital images, results of the analysis of the digital images, metrics, and the like. I/O devices 726 may also include a display including a graphical user interface (GUI) for outputting information on a monitor. I/O devices 726 may also include peripheral devices such as, for example, a printer for printing information associated with the computer, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 727 may include one or more components configured to transmit and receive data via a communication network, such as the Internet, a local area network, a workstation peer-to-peer network, a direct link network, a wireless network, or any other suitable communication platform. For example, interface 727 may include one or more modulators, demodulators, multiplexers, demultiplexers, network communication devices, wireless devices, antennas, modems, and any other type of device configured to enable data communication via a communication network.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process.

Experimental Setup 150-pair images (see Table 1) were selected from normal and abnormal (effusion and tympanostomy tube) categories, which have the highest number of paired images in the dataset described above. Even after the dataset was enhanced with selected video frames of the videos, the dataset contained 150 paired eardrum images to train the model. Even though it is known that the balanced amount of data for each category would avoid the bias towards the majority classes and minimize the overall error rate, more normal-abnormal pair images could not be added to the dataset because of the limited number of cases.

The limited number of pair images was used for both training and testing groups of data. The system had two training steps: one for the transfer learning training and the other for the random forest classifier training. A separate validation dataset was used for transfer learning training, which contained single 83 'normal' and 54 'abnormal' eardrum images (not pairs), during the retraining of the lookup table generation feature extraction phase. Because a separate dataset was used for validation, more cases could not be allocated for training.

To test the generalizability of our results, a k-fold (k=3) cross-validation was used. Since the number of 'normal-abnormal' and 'abnormal-normal' pair images was low, the fold number (k) was also kept low. The paired images were divided into three random groups for each category: one group was used for testing, and the other two groups were used for training. The training group was used to learn the network parameters in transfer learning and fit a model for the tree bagger classifier part. Because the data were divided into groups before the system was run, the same pair was put in the same group, either in training or testing. So, each patient's eardrum image pairs were used for either training or testing, but not both.

The tree bagger algorithm was also evaluated with a three-fold cross-validation method. To properly model the system, the size of the dataset and the number of categories play an important role in the tree bagger classifier. Because 100 pairs were used for training and 50 pairs were used for testing and the number of categories was four (N-N, N-A, A-A, A-N), it was empirically decided to use five trees to model the classifier.

Results and Discussion

Single eardrum images were used to train and test the system for the transfer learning part of the training with classification accuracy as a measure for each training fold. The transfer learning was retrained for extracting the lookup table values twice: before and after adding normal-abnormal image pairs. Because the number of 'normal-abnormal' pair images was limited, we started with 'normal-normal' and 'abnormal-abnormal' pair images and with the classification categories of normal or abnormal. Then, the experiments were performed adding 'normal-abnormal' eardrum pair images and compared them. Table 2 shows these two experimental results for these cases.

TABLE 2

Transfer learning classification accuracies
for single images as normal or abnormal

| | Before normal-abnormal cases added | | | After normal-abnormal cases added | | |
|---|---|---|---|---|---|---|
| | Training | Validation | Testing | Training | Validation | Testing |
| Fold 1 | 89.1% | 86.7% | 80.3% | 76.3% | 82.4% | 78.8% |
| Fold 2 | 85.4% | 93.3% | 82.9% | 86.8% | 70.6% | 78.8% |
| Fold 3 | 92.0% | 80.0% | 86.8% | 87.6% | 82.4% | 78.6% |
| Average | 88.8% | 86.7% | 83.3% | 83.6% | 78.4% | 78.7% |
| Standard Deviation | 3.3% | 6.7% | 3.3% | 6.3% | 6.8% | 0.1% |

As shown in Table 2, before adding normal-abnormal pairs' eardrum images, training, validation, and testing accuracies were 88.8%±3.3%, 86.7%±6.7%, and 83.3%±3.3%, respectively. However, adding normal-abnormal cases decreased accuracies for to 83.6%±6.3%, 78.4%±6.8% and 78.7%±0.1%. This training step was used just for creating a lookup table and extracting lookup table features.

After creating the lookup table with transfer learning, we experimentally tested the lookup table-based feature extraction and handcrafted feature extraction. Lookup table based feature extraction was the first step of the feature extraction phase. The handcrafted features were registration errors, the number of counts in bins of the histogram of L*a*b*, mean, and other statistical measurements (standard deviation, skewness, and kurtosis), and these were concatenated in each step, and the system was tested after each concatenation.

Figure 8:
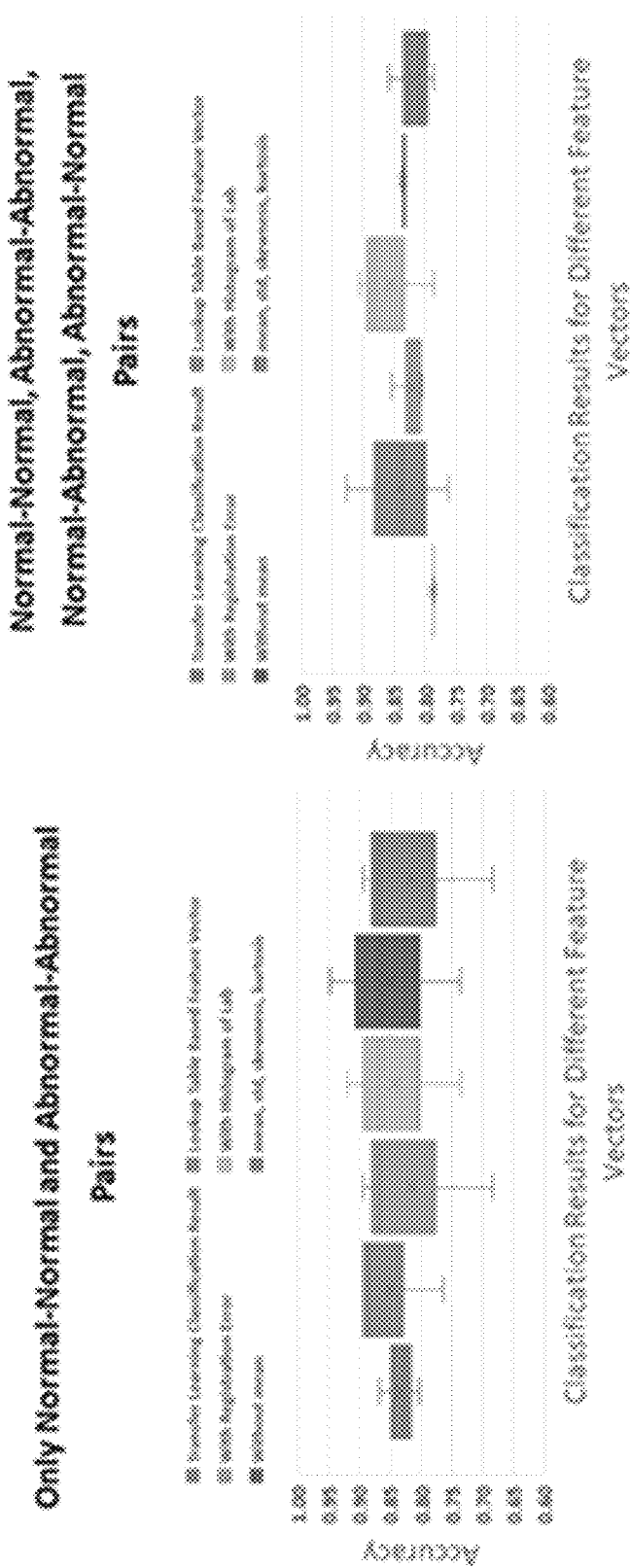
FIG. 8 illustrates results of three-fold classification accuracies for different feature vectors only normal-normal and abnormal-abnormal pairs and after added abnormal-normal/normal-abnormal pairs.

FIG. 8 presents system accuracies for normal-normal (N-N), abnormal-abnormal (A-A), and all pairs (N-N, A-A, N-A, and A-N). After adding N-A, A-N pair images, the accuracies decreased. Before the N-A pairs added to the dataset, lookup table based feature extraction accuracy result was the highest accuracy with 85.1% and 7.6% low standard deviation. After adding A-N pairs, the highest accuracy result was 85.8%±6.4% for concatenated registration error and histogram of L*a*b* features to the lookup table based features.

When the paired image classification accuracies are compared with those of the single images, some improvements were observed from 83.3% (SD±3.3%) to 85.1% (SD±7.6%) (N-N and A-A pairs) and from 78.8% (SD±0.1%) to 85.8 (SD±6.4%) (N-N, A-A, N-A, and A-N pairs). Unfortunately, most of the improvements are not statistically significant according to the t-test between the classification results of transfer learning and each tested pair features. For the same category pair (i.e., N-N and A-A) images, the average p-value is 0.80, while for all category pair (N-N, A-A, N-A, and A-N) images, the average p-value is 0.16. While the p-values decreased, they were not statistically significant (<0.05). However, the p-value of the t-test between the classification results of transfer learning and all features (except the mean value of the L*a*b* color space) is 0.0004, which is statistically significant. The reason is standard deviations of both results for three-fold cross-validation are 0.1%, and 0.2%, while their accuracy values are 78.7% and 83.3%, respectively. So, all three-fold results were consistent with just for small differences.

Figure 9A:
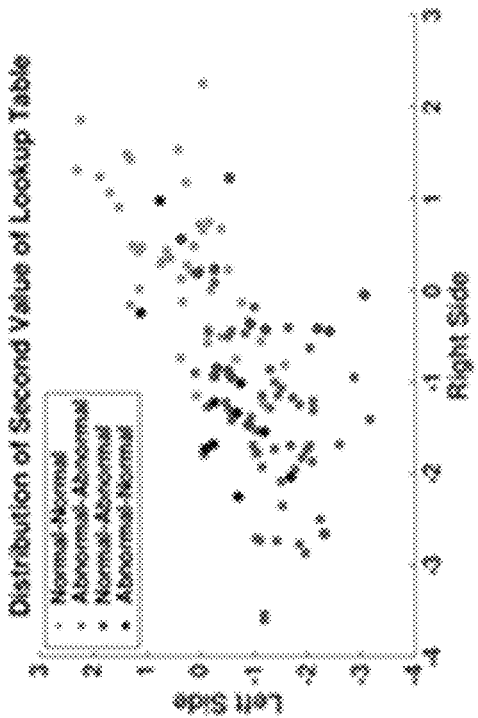
FIGS. 9A and 9B illustrate lookup value distribution of right and left side of eardrum for normal-normal, abnormal-abnormal, normal-abnormal, and abnormal-normal pairs.
Figure 9B:
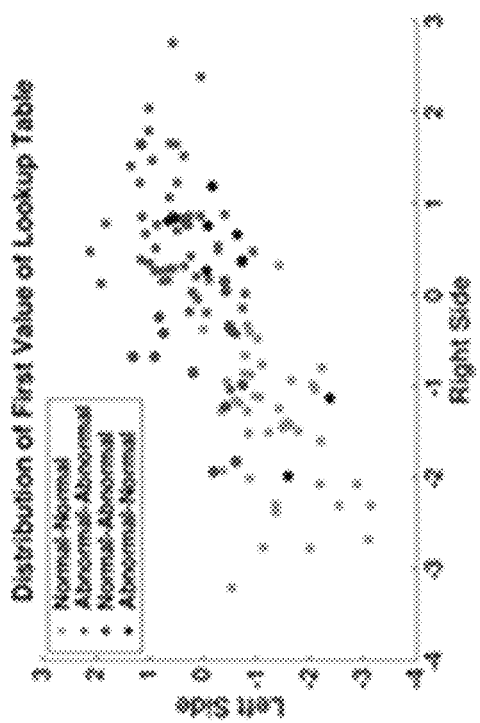

FIGS. 9A and 9B illustrate lookup value distribution of right and left side of eardrum for normal-normal, abnormal-abnormal, normal-abnormal, and abnormal-normal pairs. While normal-normal pairs first lookup table values located in the lower-left corner and abnormal-abnormal pairs first lookup table values located in the upper-right corner of FIG. 9A, and vice versa for FIG. 9B. The first values of right and left normal pairs (N-N) were less than zero, and for abnormal pairs (A-A), the same values were greater than −0.5 (FIG. 9A). For the second lookup table values, N-N and A-A pair corners switched (FIG. 9B). The expectation was Normal-Abnormal pairs would state on the upper-left, and Abnormal-Normal pairs would state on the lower-right corner of FIG. 9A, and vice versa for FIG. 9B. However, normal-abnormal and abnormal-normal pairs stated mixed into other pairs. The number of normal-abnormal and abnormal-normal pairs are very limited, and most of them are subtle.

In FIGS. 9A and 9B, because N-N and A-A pair distributions were well separated into separate quadrants of the feature space, our expectation was the normal-abnormal pair values distribute to the other quadrants. For example, in FIG. 9A, N-N pairs both right and left values less than 0, A-A pairs values greater than −0.5, and A-N (ear pair right side abnormal and left side normal) pairs (represented with a black circle) are supposed to distribute to the lower-right quadrant of the figure. Likewise, for N-A (ear pair right side normal and left side abnormal) pairs (represented with blue circle) are supposed to distribute to the upper-left quadrant of FIG. 9A. However, black and blue circles mixed in N-N and A-A pair values are in FIGS. 9A and 9B. This caused decreasing in the accuracies for transfer learning test results and lookup table based feature extraction system results after adding normal-abnormal pair images.

Figure 10:
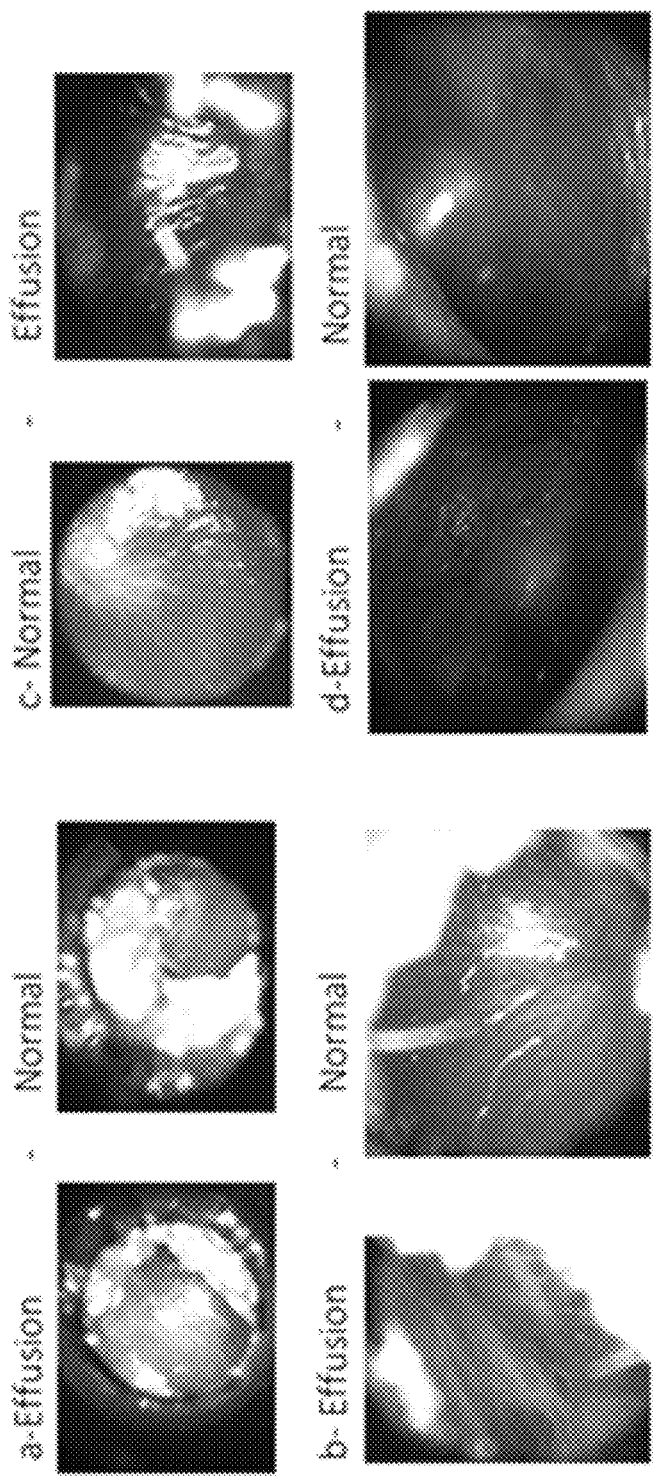
FIG. 10 illustrates four examples about pair images, which were labeled as 'subtle' by an ENT specialist and misclassified by transfer learning.

After these unexpected distributions of blue (i.e., N-A) and black circles (i.e., A-N) were observed, an ENT expert examined the normal-abnormal pair images, which were selected from video frames of both adult and pediatric patients' otoscope video clip. He labeled the normal-abnormal pair images as 'subtle' or 'not subtle,' and 63.3% (19/30) of the pair images were labeled as 'subtle.' FIG. 10 illustrates four examples about pair images which were labeled as 'subtle' by our ENT specialist and misclassified by transfer learning.

Imaging problems may be the reason for misclassification. Three pairs had illumination problems which manifest themselves on images as yellow or white light spots, making it difficult for the camera to focus on the eardrum region. Another common problem was ear wax and hairs because they were closer than the eardrum to the otoscope, reflecting light. Furthermore, the eardrum region of the image was not enough to classify its category. Another problem with these images was the blurry parts of the images. The second column of FIG. 10 demonstrates images with out of focus problems. While FIG. 10c-Normal is an in-focus image, FIG. 10c-Effusion is blurry between the two regions with light reflections. In contrast, FIG. 10d-Effusion and 10d-Normal contain blurry regions regardless of the amount of light reflection.

Depending on the problems (light, wax, hair, or blurring) of the normal-abnormal pairs' images, the accuracy decreases. However, we wanted to experimentally test and investigate the normal-abnormal cases with a limited amount of data. While the improvements in accuracies are not statistically significant (most likely because of limited data), we still observed an increase in them using our approach, and this increase could likely be due to additional features that are extracted from the paired images and used together. Our paired image classification approach is the first for classifying pair eardrum images together, and the results are promising.

Conclusions

In this study, we propose a system to classify pair eardrum images together as 'normal-normal,' 'abnormal-abnormal,' 'normal-abnormal,' and 'abnormal-normal.' To the best of our knowledge, this is the first study that classifies a pair of eardrum images of the same patient together. To classify the pair of images, we used two feature extraction methods: deep learning-based and handcrafted, and combined the resulting features of two sides of eardrum images to classify the pair of images together. Then, we analyzed the results of one side of eardrum images and pair eardrum images with and without 'normal-abnormal' and 'abnormal-normal' cases.

We also compared the results after extracting each group of features of the paired images. According to the experimental results, the highest accuracy was 85.8% (±6.4%) for all types of pair image classification. The features of concatenated registration error and histogram of L*a*b* features. But the only statistically significant result of the difference between single side eardrum image classification with transfer learning was due to all the extracted and concatenated features (without the feature of the mean of L*a*b* color space) with 83.5% (±0.2%) accuracy. Other experiments did not create any statistically significant difference. Still, at least one statistically significant result is promising with all concatenated features except the mean of L*a*b* color space features.

One of the study's limitations is the small number of A-N (abnormal-normal) paired images, and the abnormal class comprises only of otitis media effusion and tympanostomy tube categories. In addition to this, 63.3% (19/30) of the existing A-N pair images were subtle as assessed by a specialist. Future studies will include a larger number of pair images for each category of eardrum pairs. We also observed that transfer learning based lookup table values for the same category pairs could be classified easily according to differently labeled pair images. Therefore, we can use the lookup table values to select subtle images and automatically eliminate them from the training dataset for future studies.

REFERENCES

Each of the below references is individually incorporated by reference and made a part hereof:

[1] L. K. Cole, "Otoscopic evaluation of the ear canal," The Veterinary clinics of North America. Small animal practice, vol. 34, no. 2, pp. 397-410, 2004.

[2] M. E. Pichichero and M. D. Poole, "Comparison of performance by otolaryngologists, pediatricians, and general practitioners on an otoendoscopic diagnostic video examination," International journal of pediatric otorhinolaryngology, vol. 69, no. 3, pp. 361-366, 2005.

[3] L. S. Goggin, R. H. Eikelboom, and M. D. Atlas, "Clinical decision support systems and computer-aided diagnosis in otology," Otolaryngology—Head and Neck Surgery, vol. 136, no. 4_suppl, pp. s21-s26, 2007.

[4] M. A. Khan et al., "Automatic detection of tympanic membrane and middle ear infection from oto-endoscopic images via convolutional neural networks," Neural Networks, 2020.

[5] A. Kuruvilla, N. Shaikh, A. Hoberman, and J. Kovačević, "Automated diagnosis of otitis media: vocabulary and grammar," International Journal of Biomedical Imaging, vol. 2013, 2013.

[6] E. Başaran, Z. Cömert, and Y. Çelik, "Convolutional neural network approach for automatic tympanic membrane detection and classification," Biomedical Signal Processing and Control, vol. 56, p. 101734, 2020.

[7] M. S. Kasher, "Otitis Media Analysis—An Automated Feature Extraction and Image Classification System," 2018.

[8] E. Başaran, Z. Cömert, A. Şengür, Ü. Budak, Y. Çelik, and M. Toğaçar, "Chronic Tympanic Membrane Diagnosis based on Deep Convolutional Neural Network," in 2019 4th International Conference on Computer Science and Engineering (UBMK), 2019: IEEE, pp. 1-4.

[9] H. C. Myburgh, S. Jose, D. W. Swanepoel, and C. Laurent, "Towards low cost automated smartphone- and cloud-based otitis media diagnosis," Biomedical Signal Processing and Control, vol. 39, pp. 34-52, 2018.

[10] L. Monasta et al., "Burden of disease caused by otitis media: systematic review and global estimates," PloS one, vol. 7, no. 4, p. e36226, 2012.

[11] D. Cha, C. Pae, S.-B. Seong, J. Y. Choi, and H.-J. Park, "Automated diagnosis of ear disease using ensemble deep learning with a big otoendoscopy image database," E Bio Medicine, vol. 45, pp. 606-614, 2019.

[12] C. Senaras et al., "Autoscope: automated otoscopy image analysis to diagnose ear pathology and use of clinically motivated eardrum features," in Medical Imaging 2017: Computer-Aided Diagnosis, 2017, vol. 10134: International Society for Optics and Photonics, p. 101341X.

[13] H. Binol et al., "Decision fusion on image analysis and tympanometry to detect eardrum abnormalities," in Medical Imaging 2020: Computer-Aided Diagnosis, 2020, vol. 11314: International Society for Optics and Photonics, p. 113141M.

[14] C.-K. Shie, H.-T. Chang, F.-C. Fan, C.-J. Chen, T.-Y. Fang, and P.-C. Wang, "A hybrid feature-based segmentation and classification system for the computer aided self-diagnosis of otitis media," in 2014 36th Annual International Conference of the IEEE Engineering in Medicine and Biology Society, 2014: IEEE, pp. 4655-4658.

[15] M. Viscaino, J. C. Maass, P. H. Delano, M. Torrente, C. Stott, and F. Auat Cheein, "Computer-aided diagnosis of external and middle ear conditions: A machine learning approach," Plos one, vol. 15, no. 3, p. e0229226, 2020.

[16] J. Seok, J.-J. Song, J.-W. Koo, H. C. Kim, and B. Y. Choi, "The semantic segmentation approach for normal and pathologic tympanic membrane using deep learning," BioRxiv, p. 515007, 2019.

[17] H. Binol et al., "Digital otoscopy videos versus composite images: A reader study to compare the accuracy of ENT physicians," The Laryngoscope, 2020.

[18] H. Binol et al., "SelectStitch: automated frame segmentation and stitching to create composite images from Otoscope video clips," Applied Sciences, vol. 10, no. 17, p. 5894, 2020.

[19] S. Camalan et al., "OtoMatch: Content-based eardrum image retrieval using deep learning," Plos one, vol. 15, no. 5, p. e0232776, 2020.

[20] C.-K. Shie, H.-T. Chang, F.-C. Fan, C.-J. Chen, T.-Y. Fang, and P.-C. Wang, "A hybrid feature-based segmentation and classification system for the computer aided self-diagnosis of otitis media," in Engineering in Medicine and Biology Society (EMBC), 36th Annual International Conference of the IEEE, 2014 2014, pp. 4655-4658.

[21] I. Mironică, C. Vertan, and D. C. Gheorghe, "Automatic pediatric otitis detection by classification of global image features," in 2011 E-Health and Bioengineering Conference (EHB), 2011: IEEE, pp. 1-4.

[22] E. Başaran, A. Şengür, Z. Cömert, Ü. Budak, Y. Çelik, and S. Velappan, "Normal and Acute Tympanic Membrane Diagnosis based on Gray Level Co-Occurrence Matrix and Artificial Neural Networks," in 2019 International Artificial Intelligence and Data Processing Symposium (IDAP), 2019: IEEE, pp. 1-6.

[23] A. Kuruvilla, N. Shaikh, A. Hoberman, and J. Kovačević, "Automated Diagnosis of Otitis Media: Vocabulary and Grammar," (in en), International Journal of Biomedical Imaging, pp. 1-15, 2013 2013, doi: 10.1155/2013/327515.

[24] C. Senaras et al., "Detection of eardrum abnormalities using ensemble deep learning approaches," in Medical Imaging 2018: Computer-Aided Diagnosis, 2018, vol. 10575: International Society for Optics and Photonics, p. 105751A.

[25] J. Y. Lee, S.-H. Choi, and J. W. J. A. S. Chung, "Automated Classification of the Tympanic Membrane Using a Convolutional Neural Network," vol. 9, no. 9, p. 1827, 2019.

[26] L. G. Brown, "A survey of image registration techniques," ACM computing surveys (CSUR), vol. 24, no. 4, pp. 325-376, 1992.

[27] S. Mambo, Y. Hamam, B. van Wyk, K. Djouani, and P. Siarry, "A review on medical image registration techniques," World Academy of Science, Engineering and Technology International Journal of Computer and Information Engineering, vol. 12, no. 1, 2018.

[28] X. Huang, J. Ren, G. Guiraudon, D. Boughner, and T. M. Peters, "Rapid dynamic image registration of the beating heart for diagnosis and surgical navigation," IEEE transactions on medical imaging, vol. 28, no. 11, pp. 1802-1814, 2009.

[29] K. Miller et al., "Modelling brain deformations for computer-integrated neurosurgery," International Journal for Numerical Methods in Biomedical Engineering, vol. 26, no. 1, pp. 117-138, 2010.

[30] N. Strehl, S. Tomei, J. Rosenman, and S. Joshi, "Large deformation 3D image registration in image-guided radiation therapy."

[31] D. Maksimov et al., "Graph-matching based CTA," IEEE transactions on medical imaging, vol. 28, no. 12, pp. 1940-1954, 2009.

[32] A. Roche, X. Pennec, G. Malandain, and N. J. I. t. o. m. i. Ayache, "Rigid registration of 3-D ultrasound with MR images: a new approach combining intensity and gradient information," vol. 20, no. 10, pp. 1038-1049, 2001.

[33] J.-P. Thirion, "Non-rigid matching using demons," in Proceedings CVPR IEEE Computer Society Conference on Computer Vision and Pattern Recognition, 1996: IEEE, pp. 245-251.

[34] A. Keikhosravi, B. Li, Y. Liu, and K. W. Eliceiri, "Intensity-based registration of bright-field and second-harmonic generation images of histopathology tissue sections," Biomedical Optics Express, vol. 11, no. 1, pp. 160-173, 2020.

[35] M. Styner, C. Brechbuhler, G. Szckely, and G. Gerig, "Parametric estimate of intensity inhomogeneities applied to MM," IEEE transactions on medical imaging, vol. 19, no. 3, pp. 153-165, 2000.

[36] D.-J. Kroon, "Multimodality non-rigid demon algorithm image registration," MatlabCentral, www.math-works.com/matlabcentral/fileexchange/21451-multimo-dality-non-rigid-demon-algorithm-imageregistration, 2008.

[37] L. Breiman, "Bagging predictors," Machine learning, vol. 24, no. 2, pp. 123-140, 1996.

[38] W. Matthew, "Bias of the Random Forest out-of-bag (OOB) error for certain input parameters," Open Journal of Statistics, vol. 2011, 2011.

[39] G. James, D. Witten, T. Hastie, and R. Tibshirani, An introduction to statistical learning. Springer, 2013.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby fully incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method of classifying tympanic membrane pathologies from images of both a left and a right tympanic membrane of a subject, comprising:
    capturing one or more images of each of a left tympanic membrane and one or more images of a right tympanic membrane of a subject using an image capture device;
    performing preprocessing and data augmentation on the captured one or more images of the left tympanic membrane and the right tympanic membrane;
    registering each of the one or more images of the left tympanic membrane with a corresponding one of the one or more images of the right tympanic membrane, wherein image registration calculates a registration error between the pair of eardrum images and is used as a feature to classify pairs of images of the left tympanic membrane and the right tympanic membrane together to form pairs of registered eardrum images of the subject;
    extracting additional features from both images of each of the pairs of registered eardrum images;
    forming a single feature vector for each of the pairs of registered eardrum images using all the extracted features including the registration error between the pair of registered eardrum images; and classifying pathologies of the pair of registered eardrum images using the single feature vector for each of the pairs of registered eardrum images.

2. The method of claim 1, wherein the feature vector has two parts, a first part comprised of lookup table-based values created by using deep learning techniques, and a second part comprised of handcrafted features created by recording the registration errors between each of the pairs of registered eardrum images, color-based features such as histogram of a* and b* component of the L*a*b* color space, and statistical measurements of these color channels.

3. The method of claim 2, wherein the deep learning techniques include transfer-based learning.

4. The method of claim 3, wherein the transfer-based learning comprises retraining deep learning networks including Inception V3 or ResNet.

5. The method of claim 1, wherein the extracted features are concatenated to form the single feature vector, and wherein classifying pathologies of the pairs of registered eardrum images comprises classifying the single feature vector by a tree bagger classifier.

6. The method of claim 1, wherein preprocessing further includes one or more of reducing sensor based problems, selecting a region of interest in the one or more images, detecting glare effects (light reflections), wax, hair, dark margins, and text and creating a copy of the one or more images where the glare effects, wax, hair, dark margins and text are reduced or removed from the composite image of the right tympanic membrane and the composite image of the corresponding left tympanic membrane of the subject, and wherein data augmentation includes reflecting each of the one or more images both horizontally and vertically, scaling each of the one or more images in the range of 0.7 to 2, rotating each of the one or more images randomly, shearing each of the one or more images both horizontally and vertically within a range of 0 to 45 degrees, and translating them within a pixel range from −30 to 30 pixels in both horizontal and vertical directions.

7. The method of claim 1, wherein classifying pathologies of the pair of eardrum images comprises classifying each eardrum as normal or abnormal, wherein the abnormalities include one or more of acute otitis media (AOM), middle ear effusion (non-infected fluid), cholesteatoma (a common destructive skin cyst in the ear), eardrum perforation, and eardrum retraction vs normal.

8. The method of claim 1, wherein the image capture device comprises a high-resolution otoscope or a digital video-otoscope configured to capture one or more still images of each of the tympanic membranes or capture a video of each of the tympanic membranes.

9. A system for classifying tympanic membrane pathologies from images of both a left and a right tympanic membrane of a subject, comprising:
an image capture device, wherein the image capture device captures one or more images of each of a left tympanic membrane and one or more images of a right tympanic membrane of a subject;
a memory, wherein the captured one or more images of each of a left tympanic membrane and one or more images of a right tympanic membrane of a subject are stored; and
a processor in communication with the memory, wherein the processor executes computer-readable instructions stored in the memory that cause the processor to;

perform preprocessing and data augmentation on the captured one or more images of the left tympanic membrane and the right tympanic membrane;
registering each of the one or more images of the left tympanic membrane with a corresponding one of the one or more images of the right tympanic membrane, wherein image registration calculates a registration error between the pair of eardrum images and is used as a feature to classify pairs of images of the left tympanic membrane and the right tympanic membrane together to form pairs of registered eardrum images of the subject;
extract additional features from both images of each of the pairs of registered eardrum images;
form a single feature vector for each of the pairs of registered eardrum images using all the extracted features including the registration error between the pair of registered eardrum images; and
classify pathologies of the pairs of registered eardrum images using the single feature vector for each of the pairs of registered eardrum images.

10. The system of claim 9, wherein the feature vector has two parts, a first part comprised of lookup table-based values created by using deep learning techniques, and a second part comprised of handcrafted features created by recording the registration errors between each of the pairs of registered eardrum images, color-based features such as histogram of a* and b* component of the L*a*b* color space, and statistical measurements of these color channels.

11. The system of claim 10, wherein the deep learning techniques include transfer-based learning.

12. The system of claim 11, wherein the transfer-based learning comprises retraining deep learning networks including Inception V3 or ResNet.

13. The system of claim 9, wherein the extracted features are concatenated to form the single feature vector, and wherein classifying pathologies of the pair of registered eardrum images comprises classifying the single feature vector by a tree bagger classifier.

14. The system of claim 9, wherein preprocessing includes one or more of reducing sensor based problems, selecting a region of interest in the one or more images, detecting glare effects (light reflections), wax, hair, dark margins, and text and creating a copy of the one or more images where the glare effects, wax, hair, dark margins and text are reduced or removed from the composite image of the right tympanic membrane and the composite image of the corresponding left tympanic membrane of the subject, and wherein data augmentation includes reflecting each of the one or more images both horizontally and vertically, scaling each of the one or more images in the range of 0.7 to 2, rotating each of the one or more images randomly, shearing each of the one or more images both horizontally and vertically within a range of 0 to 45 degrees, and translating them within a pixel range from −30 to 30 pixels in both horizontal and vertical directions.

15. The system of claim 9, wherein classifying pathologies of the pair of eardrum images comprises classifying each eardrum as normal or abnormal, wherein the abnormalities include one or more of acute otitis media (AOM), middle ear effusion (non-infected fluid), cholesteatoma (a common destructive skin cyst in the ear), eardrum perforation, and eardrum retraction vs normal.

16. The system of claim 9, wherein the image capture device comprises a high-resolution otoscope or a digital video-otoscope configured to capture one or more still images of each of the tympanic membranes or capture a video of each of the tympanic membranes.

17. A non-transitory computer-program product comprising computer executable code sections stored on a computer-readable medium, said computer executable code sections for performing a method of classifying tympanic membrane pathologies from images, comprising:
receiving one or more images of each of a left tympanic membrane and one or more images of a right tympanic membrane of a subject;
performing preprocessing and data augmentation on the one or more images of the left tympanic membrane and the right tympanic membrane;
registering each of the one or more images of the left tympanic membrane with a corresponding one of the one or more images of the right tympanic membrane, wherein image registration calculates a registration error between the pair of eardrum images and is used as a feature to classify pairs of images of the left tympanic membrane and the right tympanic membrane together to form pairs of registered eardrum images of the subject;
extracting additional features from both images of each of the pairs of registered eardrum images;
forming a single feature vector for each of the pairs of registered eardrum images using all the extracted features including the registration error between the pair of registered eardrum images; and
classifying pathologies of the pairs of registered eardrum images using the single feature vector for each of the pairs of registered eardrum images.

18. The computer-program product of claim 17, wherein the feature vector has two parts, a first part comprised of lookup table-based values created by using deep learning techniques, and a second part comprised of handcrafted features created by recording the registration errors between each of the pairs of registered eardrum images, color-based features such as histogram of a* and b* component of the L*a*b* color space, and statistical measurements of these color channels.

19. The computer-program product of claim 18, wherein the deep learning techniques include transfer-based learning.

20. The computer-program product of claim 19, wherein the transfer-based learning comprises retraining deep learning networks including Inception V3 or ResNet.

21. The computer-program product of claim 17, wherein the extracted features are concatenated to form the single feature vector, and wherein classifying pathologies of the pair of registered eardrum images comprises classifying the single feature vector by a tree bagger classifier.

22. The computer-program product of claim 17, wherein preprocessing includes one or more of reducing sensor based problems, selecting a region of interest in the one or more images, detecting glare effects (light reflections), wax, hair, dark margins, and text and creating a copy of the one or more images where the glare effects, wax, hair, dark margins and text are reduced or removed from the composite image of the right tympanic membrane and the composite image of the corresponding left tympanic membrane of the subject, and wherein data augmentation includes reflecting each of the one or more images both horizontally and vertically, scaling each of the one or more images in the range of 0.7 to 2, rotating each of the one or more images randomly, shearing each of the one or more images both horizontally and vertically within a range of 0 to 45 degrees, and translating them within a pixel range from −30 to 30 pixels in both horizontal and vertical directions.

23. The computer-program product of claim 17, wherein classifying pathologies of the pair of eardrum images comprises classifying each eardrum as normal or abnormal, wherein the abnormalities include one or more of acute otitis media (AOM), middle ear effusion (non-infected fluid), cholesteatoma (a common destructive skin cyst in the ear), eardrum perforation, and eardrum retraction vs normal.

24. The computer-program product of claim 17, wherein an image capture device comprising a high-resolution otoscope or a digital video-otoscope is configured to capture one or more still images of each of the tympanic membranes or capture a video of each of the tympanic membranes.

25. The method of claim 1, wherein registering each of the one or more images of the left tympanic membrane with a corresponding one of the one or more images of the right tympanic membrane comprises using both rigid and non-rigid registration, wherein for both types of registration there is a target image and a moving image, said moving (source) image transforms spatially to align with the target (fixed, sensed) image.

26. The method of claim 25, wherein rigid registration includes translation, scaling, and rotation of the moving image to the target image, and non-rigid matching is done using a method that transforms points depending on Maxwell's demons and matches deformed parts of the image.

27. The system of claim 9, wherein registering each of the one or more images of the left tympanic membrane with a corresponding one of the one or more images of the right tympanic membrane comprises using both rigid and non-rigid registration, wherein for both types of registration there is a target image and a moving image, said moving (source) image transforms spatially to align with the target (fixed, sensed) image.

28. The system of claim 27, wherein rigid registration includes translation, scaling, and rotation of the moving image to the target image, and non-rigid matching is done using a method that transforms points depending on Maxwell's demons and matches deformed parts of the image.

29. The computer-program product of claim 17, wherein registering each of the one or more images of the left tympanic membrane with a corresponding one of the one or more images of the right tympanic membrane comprises using both rigid and non-rigid registration, wherein for both types of registration there is a target image and a moving image, said moving (source) image transforms spatially to align with the target (fixed, sensed) image.

30. The computer-program product of claim 29, wherein rigid registration includes translation, scaling, and rotation of the moving image to the target image, and non-rigid matching is done using a method that transforms points depending on Maxwell's demons and matches deformed parts of the image.

* * * * *